(12) United States Patent
Daniel et al.

(10) Patent No.: US 12,042,365 B2
(45) Date of Patent: Jul. 23, 2024

(54) FLUID-ABSORBENT ARTICLE

(71) Applicant: BASF SE, Ludwigshafen am Rhein (DE)

(72) Inventors: Thomas Daniel, Ludwigshafen (DE); Christophe Bauduin, Ludwigshafen (DE); Katrin Baumann, Ludwigshafen (DE); Katarzyna Dobrosielska-Oura, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 1036 days.

(21) Appl. No.: 16/482,045

(22) PCT Filed: Feb. 12, 2018

(86) PCT No.: PCT/EP2018/053418
§ 371 (c)(1),
(2) Date: Jul. 30, 2019

(87) PCT Pub. No.: WO2018/149783
PCT Pub. Date: Aug. 23, 2018

(65) Prior Publication Data
US 2020/0060897 A1 Feb. 27, 2020

(30) Foreign Application Priority Data

Feb. 17, 2017 (EP) ..................... 17156756

(51) Int. Cl.
*A61F 13/15* (2006.01)
*A61F 13/537* (2006.01)
(Continued)

(52) U.S. Cl.
CPC ............ *A61F 13/537* (2013.01); *A61L 15/60* (2013.01); *A61F 2013/530708* (2013.01)

(58) Field of Classification Search
None
See application file for complete search history.

(56) References Cited

U.S. PATENT DOCUMENTS

| 4,798,603 A | 1/1989 | Meyer et al. |
| 5,037,409 A * | 8/1991 | Chen ............... A61F 13/5376 |
| | | 604/358 |

(Continued)

FOREIGN PATENT DOCUMENTS

| DE | 3825366 A1 | 2/1989 |
| EP | 0348180 A2 | 12/1989 |

(Continued)

OTHER PUBLICATIONS

International Search Report for International Application No. PCT/EP2018/053418, mailed Mar. 15, 2018, 4 pages.

(Continued)

*Primary Examiner* — Bradley H Philips
(74) *Attorney, Agent, or Firm* — Armstrong Teasdale LLP

(57) ABSTRACT

A fluid-absorbent article includes an upper liquid-pervious layer (A), a lower liquid-impervious layer (B), a fluid-absorbent core (C) between (A) and (B) including at least 60% by weight of non-surface postcrosslinked fluid-absorbent polymer particles and not more than 40% by weight of fibrous material, based on the sum of non-surface postcrosslinked fluid-absorbent polymer particles and fibrous material. An acquisition-distribution layer (D) between (A) and (C) includes at least 90% by weight of synthetic fibers and not more than 10% by weight of cellulose based fibers, based on the sum of synthetic fibers and cellulose based fibers. The basis weight of the acquisition-distribution layer (D) is at least 70 gsm. The fluid-absorbent polymer particles have a saline flow conductivity (SFC) of less than $5 \times 10^{-7}$ cm$^3$s/g and an AUHL of less than 15 g/g. Preferably the (Continued)

Figure 1:
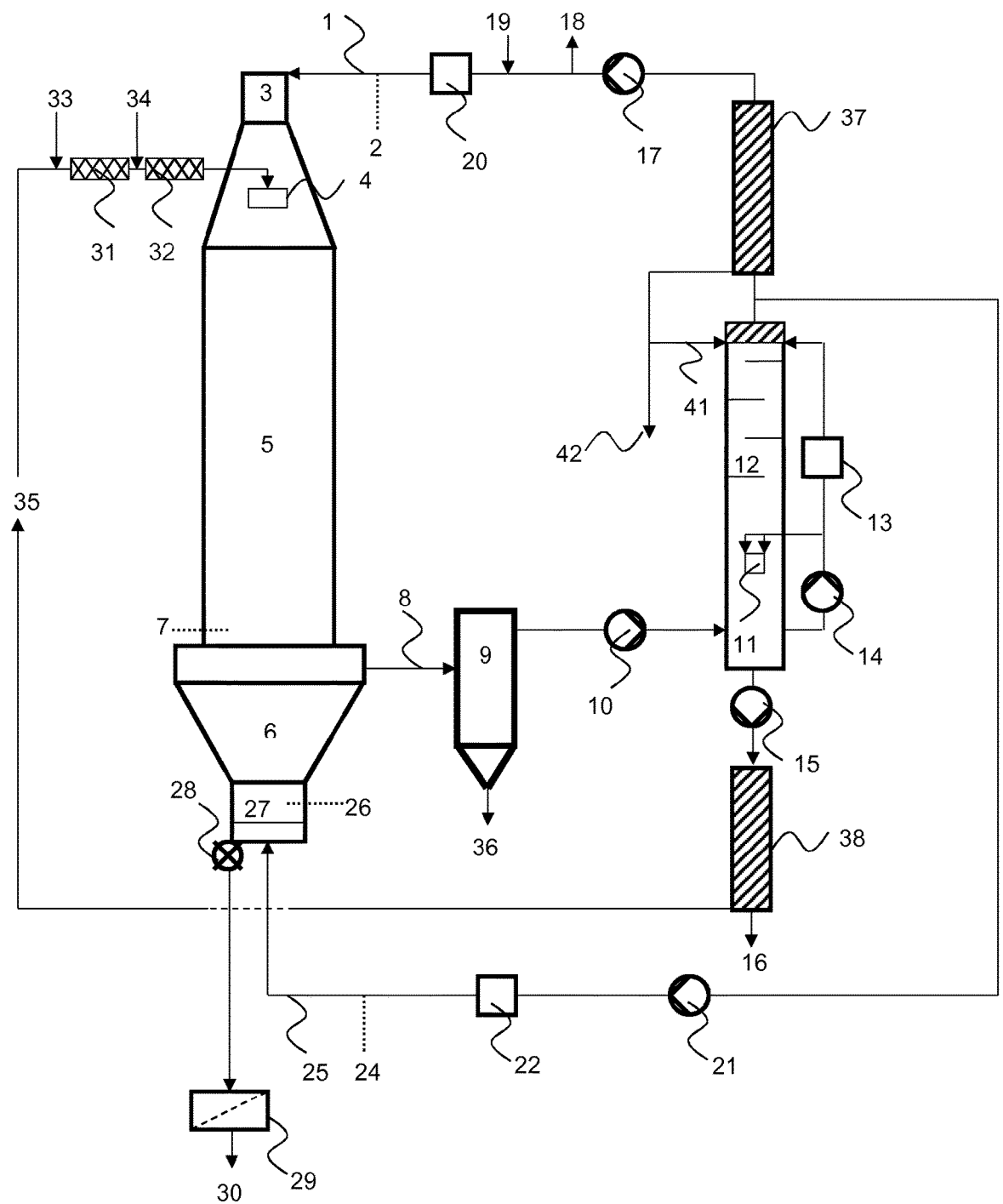

acquisition-distribution layer (D) is a non-woven web including a three dimensional network of fibers.

11 Claims, 5 Drawing Sheets

(51) Int. Cl.
*A61L 15/60* (2006.01)
*A61F 13/53* (2006.01)

(56) References Cited

U.S. PATENT DOCUMENTS

| | | | |
|---|---|---|---|
| 5,217,445 A | 6/1993 | Young et al. | |
| 5,269,980 A | 12/1993 | Levendis et al. | |
| 5,300,565 A * | 4/1994 | Berg | A61L 15/60 525/54.31 |
| 5,342,535 A * | 8/1994 | Ramirez | A61Q 15/00 510/108 |
| 5,549,791 A | 8/1996 | Herron et al. | |
| 5,599,335 A * | 2/1997 | Goldman | A61L 15/42 604/378 |
| 5,733,273 A * | 3/1998 | Ahr | A61F 13/53717 604/378 |
| 5,800,418 A * | 9/1998 | Ahr | A61F 13/15203 604/374 |
| 5,827,254 A * | 10/1998 | Trombetta | A61F 13/53418 604/378 |
| 5,866,173 A * | 2/1999 | Reiter | A61F 13/532 425/134 |
| 6,184,271 B1 | 2/2001 | Westland et al. | |
| 6,241,928 B1 | 6/2001 | Hatsuda et al. | |
| 6,972,011 B2 | 12/2005 | Maeda et al. | |
| 7,378,568 B2 | 5/2008 | Thomas et al. | |
| 8,235,957 B2 | 8/2012 | Anatolyevna et al. | |
| 9,789,011 B2 | 10/2017 | Roe et al. | |
| 2002/0004654 A1* | 1/2002 | Daniels | A61F 13/511 604/366 |
| 2005/0165208 A1* | 7/2005 | Popp | C08G 65/3322 528/300 |
| 2005/0176910 A1 | 8/2005 | Jaworek et al. | |
| 2011/0162989 A1 | 7/2011 | Ducker et al. | |
| 2011/0238026 A1* | 9/2011 | Zhang | A61F 13/534 604/372 |
| 2011/0270204 A1 | 11/2011 | Fukudome et al. | |
| 2017/0266336 A1 | 9/2017 | Gande et al. | |
| 2017/0281422 A1 | 10/2017 | Herfert et al. | |
| 2017/0281425 A1 | 10/2017 | Herfert et al. | |
| 2018/0030218 A1 | 2/2018 | Mark et al. | |
| 2018/0043052 A1 | 2/2018 | Bauer et al. | |
| 2018/0044486 A1 | 2/2018 | Bauer et al. | |
| 2018/0126032 A1 | 5/2018 | Mark et al. | |

FOREIGN PATENT DOCUMENTS

| | | |
|---|---|---|
| EP | 0427316 A2 | 5/1991 |
| EP | 0427317 A2 | 5/1991 |
| EP | 0429112 A2 | 5/1991 |
| EP | 0951913 A1 | 10/1999 |
| EP | 2301499 A1 | 3/2011 |
| EP | 2314264 A1 | 4/2011 |
| EP | 2387981 A1 | 11/2011 |
| EP | 2486901 A1 | 8/2012 |
| EP | 2524679 A1 | 11/2012 |
| EP | 2524680 A1 | 11/2012 |
| EP | 2535698 A1 | 12/2012 |
| EP | 2565031 A1 | 3/2013 |
| JP | 2008113857 A | 5/2008 |
| JP | 2009508620 A | 3/2009 |
| JP | 2016530961 A | 10/2016 |
| WO | 9640427 A1 | 12/1996 |
| WO | 9827262 A1 | 6/1998 |
| WO | 0138402 A1 | 5/2001 |
| WO | 2008009580 A1 | 1/2008 |
| WO | 2008040715 A2 | 4/2008 |
| WO | 2008052971 A1 | 5/2008 |
| WO | 2008086976 A1 | 7/2008 |
| WO | 2010004894 A1 | 1/2010 |
| WO | 2010004895 A1 | 1/2010 |
| WO | 2010015561 A1 | 2/2010 |
| WO | 2010076857 A1 | 7/2010 |
| WO | 2010082373 A1 | 7/2010 |
| WO | 2010118409 A1 | 10/2010 |
| WO | 2010133529 A2 | 11/2010 |
| WO | 2010143635 A1 | 12/2010 |
| WO | 2011026876 A1 | 3/2011 |
| WO | 2011084981 A1 | 7/2011 |
| WO | 2011086841 A1 | 7/2011 |
| WO | 2011086842 A1 | 7/2011 |
| WO | 2011086843 A1 | 7/2011 |
| WO | 2011086844 A1 | 7/2011 |
| WO | 2011117263 A1 | 9/2011 |
| WO | 2011117997 A1 | 9/2011 |
| WO | 2011136087 A1 | 11/2011 |
| WO | 2012048879 A1 | 4/2012 |
| WO | 2012052172 A1 | 4/2012 |
| WO | 2012052173 A1 | 4/2012 |
| WO | 2014005860 A1 | 1/2014 |
| WO | 2015028158 A1 | 3/2015 |
| WO | 2016062590 A1 | 4/2016 |
| WO | 2016134905 A1 | 9/2016 |
| WO | 2016207444 A1 | 12/2016 |
| WO | 2018029045 A1 | 2/2018 |
| WO | 2018141677 A1 | 8/2018 |

OTHER PUBLICATIONS

Written Opinion of the International Searching Authority for International Application No. PCT/EP2018/053418, mailed Mar. 15, 2018, 8 pages.
"Applications of Superabsorbent polymers", Modern Superabsorbent Polymer Technology, ed. Buchholz, et al., 1998, pp. 252-259.
European Search Report for EP Application No. 17156756.3, Issued on Jun. 19, 2017, 3 pages.
Graham, et al., "Commercial processes for the manufacture of Superabsorbent poylmers", Modern Superabsorbent Polymer Technology, ed. Buchholz, et al., 1998, pp. 69-117.

* cited by examiner

FLUID-ABSORBENT ARTICLE

CROSS-REFERENCE TO RELATED APPLICATIONS

This application is a U.S. National Phase Application of PCT/EP2018/053418, filed Feb. 12, 2018, which claims the benefit of priority to EP Application No. 17156756.3, filed Feb. 17, 2017, the contents of which are hereby expressly incorporated by reference in their entirety.

The present invention relates to a fluid-absorbent article, comprising an upper liquid-pervious layer (A), a lower liquid-impervious layer (B), a fluid-absorbent core (C) between (A) and (B) comprising at least 60% by weight of non-surface postcrosslinked fluid-absorbent polymer particles and not more than 40% by weight of fibrous material, based on the sum of non-surface postcrosslinked fluid-absorbent polymer particles and fibrous material; an acquisition-distribution layer (D) between (A) and (C) comprising at least 90% by weight of synthetic fibers and not more than 10% by weight of cellulose based fibers, based on the sum of synthetic fibers and cellulose based fibers, wherein the basis weight of the acquisition-distribution layer (D) is at least 70 gsm and
and the fluid-absorbent polymer particles have a saline flow conductivity (SFC) of less than $5 \times 10^{-7}$ cm$^3$s/g and an AUHL of less than 15 g/g.

Preferably the acquisition-distribution layer (D) is a non-woven web comprising a three dimensional network of fibers.

The preparation of water-absorbing polymer particles, which are also referred to as "fluid-absorbing polymer particles", "superabsorbent polymers", "superabsorbents" or "SAP", is likewise described in the monograph "Modern Superabsorbent Polymer Technology", F. L. Buchholz and A. T. Graham, Wiley-VCH, 1998, pages 71 to 103. The preparation of water-absorbent polymer particles by polymerizing droplets of a monomer solution is described, for example, in EP 0 348 180 A1, WO 96/40427 A1, U.S. Pat. No. 5,269,980, WO 2008/009580 A1, WO 2008/052971 A1, W02011/026876 A1, WO 2011/117263 A1, WO 2014/079694 and WO2016/134905. The so called "dropletization polymerization" affords round water-absorbent polymer particles of high mean sphericity (mSPHT). The mean sphericity is a measure of the roundness of the polymer particles and can be determined, for example, with the Camsizer® image analysis system (Retsch Technology GmbH; Haan; Germany).

The production of fluid-absorbent articles is also e.g. described in the monograph "Modern Superabsorbent Polymer Technology", F. L. Buchholz and A. T. Graham, Wiley-VCH, 1998, pages 252 to 258.

Fluid-absorbent articles typically consist of an upper liquid-pervious layer or top-sheet (A), a lower liquid-impervious layer or backsheet (B), a water-absorbing storage layer (absorbent core) (C) between layers (A) and (B), and an acquisition distribution layer (D) between layers (A) and (C).

Usually the several layers of fluid-absorbent articles fulfill definite functions such as dryness for the upper liquid-pervious layer (A), vapor permeability without wetting through for the lower liquid-impervious layer (B), a flexible, vapor permeable and thin fluid-absorbent core, showing fast absorption rates and being able to retain highest quantities of body fluids, and an acquisition-distribution layer (D) between the upper layer (A) and the core (C), acting as transport and distribution layer of the discharged body fluids.

An acquisition-distribution layer, referred to in short as ADL, is arranged underneath the top sheet. The acquisition-distribution layer usually comprises masses of fibers, i.e. chemically stiffened, twisted, curled cellulosic fibers, non-woven fibrous webs or three dimensional formed webs with apertures as e.g. generally described in U.S. Pat. No. 5,217,445 (hydrophilic ADL) and U.S. Pat. No. 4,798,603 (hydrophobic ADL) or the acquisition distribution layer (ADL) may also be made of a three dimensional formed film with apertures (e. g. U.S. Pat. No. 7,378,568).

Generally the ADL should ensure that the body liquids pass rapidly inside the structure of the absorbent article and are distributed uniformly throughout the thickness of the underlying storage layer or core instead of being absorbed in a localized manner only in the zones located underneath the points where the liquid arrives, or mainly in these zones. But often a distribution throughout the total core is not ensured.

To enable good liquid distribution subsequent developments have resulted in diapers that are made with highly permeable (fluid-permeable) SAPs. The downside of this development is that the increased permeability results in a loss of absorption capacity and typically also a reduction in absorption speed that has to be compensated by higher amounts of SAP per diaper. This contravenes the development to more economic and more sustainable products.

Furthermore highly permeable water-absorbent polymer particles usually require more steps in the production process, such as e. g. surface-postcrosslinking, and additional mechanical gel treatment to avoid slow swelling, than non-permeable SAPs. Recycling of surface-cross-linked particles (fine particles and broken larger pieces) into the gel or the finished product also effects SAP-quality negatively.

It is therefore an object of the present invention to provide fluid-absorption articles with improved fluid acquisition, absorption capacity, shorter time to dryness after a gush, and an improved general dryness.

It is also an object of the present invention to reduce the amount of SAP in the fluid-absorbent articles with no negative impact on the performance of the fluid-absorbent article.

It is furthermore an object of the present invention to provide fluid-absorption articles with improved sustainability.

To achieve this the fluid-absorbent article according to one embodiment of the invention comprising
(A) an upper liquid-pervious layer,
(B) a lower liquid-impervious layer,
(C) a fluid-absorbent core between (A) and (B) comprising at least 60% by weight of non-surface postcrosslinked fluid-absorbent polymer particles and not more than 40% by weight of fibrous material, based on the sum of fluid-absorbent polymer particles and fibrous material;
(D) an acquisition-distribution layer between (A) and (C) comprising at least 90% by weight of synthetic fibers and not more than 10% by weight of cellulose based fibers, based on the sum of synthetic fibers and cellulose based fibers,
(E) an optional tissue layer disposed immediately above and/or below (C); and
(F) other optional components,
wherein the basis weight of the acquisition-distribution layer (D) is at least 70 gsm and the fluid-absorbent polymer particles have a saline flow conductivity (SFC) of less than $5 \times 10^{-7}$ cm³s/g and an AUHL of less than 15 g/g.

Especially to improve sustainability acquisition-distribution layer, which are easily separable and recyclable are used.

According to an embodiment of the invention the basis weight of the acquisition-distribution layer (D) preferably is in a range of 70 to 180 g/m², whereas the ADL having a basis weight of at least 70 gsm, preferably at least 80 gsm, more preferably at least 90 gsm, most preferably at least 100 gsm usually not above 180 g/m².

The ADL according to an embodiment of the invention is formed by a random or preferably oriented distribution of hydrophobic fibers.

According to the invention usually the thickness of the absorbent core is higher than, preferably at least 1.2 times, the thickness of the ADL.

Figure 8:
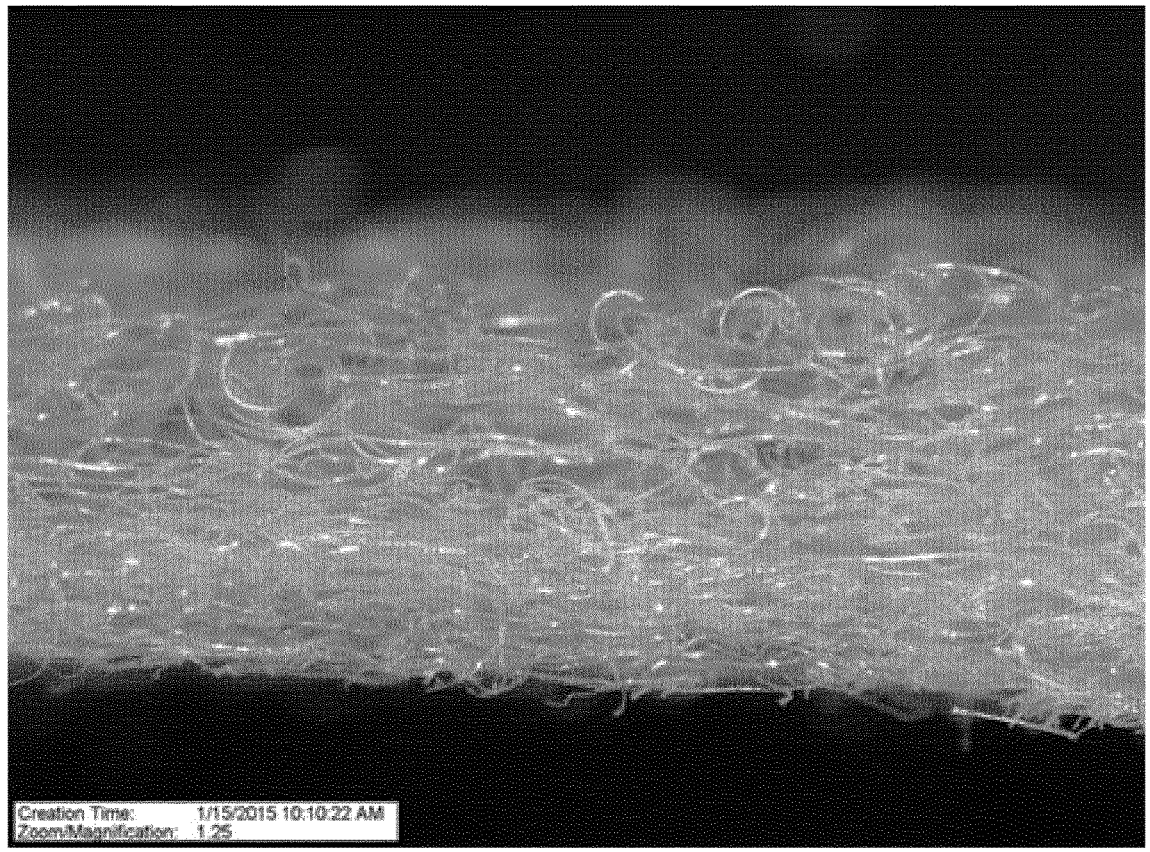

The ADL also may comprise for a good fluid management even in gush situations different hydrophobic fibers (e.g. polypropylene, polyethylene) placed in one or more than one layer or comprise more than one layer showing different porosities (e.g. comprising an upper fiber layer of a higher porosity (lower fiber density) than the adjacent fiber layer of lower porosity (higher fiber density) as e.g. shown in FIG. 8.

According to the invention it is preferred that the amount of the basis weight of the acquisition-distribution layer (D) in gsm is the same or higher than the amount of water-absorbent polymer particles contained in the fluid absorbent core (C) in % by weight, based on the sum of water-absorbent polymer particles and fibrous material.

Furthermore fluid-absorbent articles according to an embodiment of the present invention maintaining excellent dryness, independent of the absolute amounts of water-absorbent particles.

According to the invention the useful fluid-absorbent polymer particles must not be permeable but provide a high absorption capacity. This results e.g. in the possibility to provide a more sustainable fluid-absorbent article with a reduced amount of fluid-absorbent polymer particles present.

Permeability or fluid-permeability of fluid-absorbent polymer particles according to the present invention means fluid-absorbent polymer particles with an SFC of more than $20 \times 10^{-7}$ cm³s/g and/or an AUHL of at least 15 g/g.

Usually Maxi (L)-diapers contain 10 to 14 g water-absorbent particles. For the absorbent articles according to the invention even smaller amounts of water-absorbent polymers such as e.g. less than 10 g for a maxi diaper (size L), or 5 g for a midi diaper or less are sufficient. even smaller amounts of water-absorbent polymers such as e.g. less than 10 g, 9 g, 8 g or 6 g for a maxi diaper (size L), or 5 g for a midi diaper or less are sufficient.

The fluid-absorbent articles according to one embodiment of the present invention, comprising water-absorbent polymer particles and less than 15% by weight fibrous material and/or adhesives in the absorbent core.

Suitable water-absorbent polymers are produced by a process, comprising the steps forming water-absorbent polymer particles by polymerizing a monomer solution.

The level of residual monomers in the water-absorbent polymer particles have an important impact on the properties of the formed water-absorbent polymer particles.

The water-absorbent polymer particles suitable further having a level of extractable constituents of less than 20% by weight, preferably less than 15%, preferentially less than 10%, more preferably less than 8%, even more preferably less than 5% and usually not above 3%.

The fluid-absorbent polymer particles useful for the present invention are not surface-postcrosslinked (non-surface postcrosslinked water-absorbent polymer particles). The particles are only crosslinked internally.

According to one embodiment the water-absorbing particles useful in the fluid absorbent article according to the invention provide a mean sphericity or roundness of at least 0.8.

It is preferred that the water-absorbent polymer particles possess a high centrifuge retention capacity which impart good liquid absorption when used in fluid-absorbent articles. It is further preferred that the fluid-absorbent polymer particles according to one embodiment of the present invention have a centrifuge retention capacity (CRC) of typically at least 35 g/g, preferably at least 40 g/g, more preferably at least 45 g/g, most preferably at least 50 g/g and usually not above 100 g/g.

The absorbency under no load (AUNL) of the water-absorbent polymer particles according to one embodiment of the present invention is at least 35 g/g, preferably at least 40 g/g, preferentially at least 45 g/g, more preferably at least 50 g/g, even more preferably at least 55 g/g and usually not above 100 g/g.

The absorbency under high load (AUHL) of water-absorbent polymer particles useful in the invention is at least 5 g/g, but preferably less than 20 g/g, more preferably less than 15 g/g, preferentially less than 10 g/g even more preferably less than 8g/g.

Water-absorbent polymer particles according to an embodiment of the present invention have a saline flow conductivity (SFC) of less than $5 \times 10^{-7}$ cm³s/g, preferably less than $4 \times 10^{-7}$ cm³s/g, preferentially less than $3 \times 10^{-7}$ cm³s/g, more preferably less than $2 \times 10^{-7}$ cm³s/g, even more preferably less than $1 \times 10^{-7}$ cm³s/g and usually not above $0 \times 10^{-7}$ cm³s/g.

According to an embodiment of the present invention the water-absorbent polymer particles have a saline flow conductivity (SFC) of less than $5 \times 10^{-7}$ cm³s/g and a centrifuge retention capacity (CRC) of at least 35 g/g, preferably at least 40 g/g.

DETAILED DESCRIPTION OF THE INVENTION

A. Definitions

As used herein, the term "fluid-absorbent article" refers to any three-dimensional solid material being able to acquire and store fluids discharged from the body. Preferred fluid-absorbent articles are disposable fluid-absorbent articles that are designed to be worn in contact with the body of a user such as disposable fluid-absorbent pantyliners, incontinence inserts/pads, diapers, training pant diapers, breast pads, interlabial inserts/pads or other articles useful for absorbing body fluids.

As used herein, the term "fluid-absorbent composition" refers to a component of the fluid-absorbent article which is primarily responsible for the fluid handling of the fluid-absorbent article including acquisition, transport, distribution and storage of body fluids.

As used herein, the term "fluid-absorbent core" or "absorbent core" refers to a fluid-absorbent composition comprising water-absorbent polymer particles and a fibrous material, and optionally adhesive. The fluid-absorbent core is primarily responsible for the fluid handling of the fluid-absorbent article including acquisition, transport, distribution and storage of body fluids.

As used herein, the term "layer" refers to a fluid-absorbent composition whose primary dimension is along its length and width. It should be known that the term "layer" is not necessarily limited to single layers or sheets of the fluid-absorbent composition. Thus a layer can comprise laminates, composites, combinations of several sheets or webs of different materials.

As used herein the term "x-dimension" refers to the length, and the term "y-dimension" refers to the width of the fluid-absorbent composition, layer, core or article. Generally, the term "x-y-dimension" refers to the plane, orthogonal to the height or thickness of the fluid-absorbent composition, layer, core or article.

As used herein the term "z-dimension" refers to the dimension orthogonal to the length and width of the fluid absorbent composition, layer, core or article. Generally, the term "z-dimension" refers to the height of the fluid-absorbent composition, layer, core or article.

As used herein, the term "basis weight" indicates the weight of the fluid-absorbent core per square meter or of the acquisition-distribution layer per square meter respectivley. The basis weight is determined at discrete regions of the fluid-absorbent core or acquisition distribution layer respectively Further, it should be understood, that the term "upper" refers to fluid-absorbent composition which are nearer to the wearer of the fluid-absorbent article. Generally, the topsheet is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the component which is furthermost away from the wearer of the fluid-absorbent article, hereinafter described as "lower liquid-impervious layer".

As used herein, the term "liquid-pervious" refers to a substrate, layer or a laminate thus permitting liquids, i.e. body fluids such as urine, menses and/or vaginal fluids to readily penetrate through its thickness.

As used herein, the term "liquid-impervious" refers to a substrate, layer or a laminate that does not allow body fluids to pass through in a direction generally perpendicular to the plane of the layer at the point of liquid contact under ordinary use conditions.

As used herein, the term "chassis" refers to fluid-absorbent material comprising the upper liquid-pervious layer and the lower liquid-impervious layer, elastication and closure systems for the absorbent article.

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber surface, is less than 90° or when the liquid tends to spread spontaneously on the same surface.

Contrarily, term "hydrophobic" refers to fibers showing a contact angle of greater than 90° or no spontaneously spreading of the liquid across the surface of the fiber.

As used herein, the term "body fluids" refers to any fluid produced and discharged by human or animal body, such as urine, menstrual fluids, faeces, vaginal secretions and the like.

As used herein, the term "breathable" refers to a substrate, layer, film or a laminate that allows vapour to escape from the fluid-absorbent article, while still preventing fluids from leakage.

Breathable substrates, layers, films or laminates may be porous polymeric films, nonwoven laminates from spun-bond and melt- blown layers, laminates from porous polymeric films and nonwovens.

As used herein, the term "longitudinal" refers to a direction running perpendicular from a waist edge to an opposing waist edge of the fluid-absorbent article.

B. Water-Absorbent Polymer Particles

The water-absorbent polymer particles are prepared by a process, comprising the steps forming water-absorbent polymer particles by polymerizing a monomer solution, comprising a) at least one ethylenically unsaturated monomer which bears acid groups and may be at least partly neutralized, b) optionally one or more crosslinker, c) at least one initiator, d) optionally one or more ethylenically unsaturated monomers copolymerizable with the monomers mentioned under a), e) optionally one or more water-soluble polymers, f) water, and optionally coating of water-absorbent polymer particles with at least one surface-postcrosslinker and thermal surface-postcrosslinking of the coated water-absorbent polymer particles, wherein the temperature during the thermal surface-postcrosslinking is in the range from 100 to 200° C.

The water-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropane-sulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used for the inventive process.

The content of acrylic acid and/or salts thereof in the total amount of monomers a) is preferably at least 50 mol %, more preferably at least 90 mol %, most preferably at least 95 mol %.

The acid groups of the monomers a) are typically partly neutralized in the range of 0 to 100 mol %, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia or organic amines, for example, triethanolamine. It is also possible to use oxides, carbonates, hydrogencarbonates and hydroxides of magnesium, calcium, strontium, zinc or aluminum as powders, slurries or solutions and mixtures of any of the above neutralization agents. Example for a mixture is a solution of sodiumaluminate. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with water content significantly below 50% by weight may be present as a waxy material having a melting point above 23° C. In this case, metered addition as piece material or melt at elevated temperature is possible. Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tartrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylene-diaminetriacetate), and Trilon® M (methylglycinediacetic acid).

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and tri-acrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or cross-linker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, poly-ethyleneglycole diallylethers (based on polyethylene glycole having a molecular weight between 400 and 20000 g/mol), N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 18-tuply ethoxylated glycerol are particularly advantageous. Very particular preference is given to di- or tri-acrylates of 1- to 5-tuply ethoxylated and/or propoxylated glycerol. Most preferred are the tri-acrylates of 3- to 5-tuply ethoxylated and/or propoxylated glycerol and especially the triacrylate of 3-tuply ethoxylated glycerol.

The amount of crosslinker b) is preferably from 0.0001 to 0.6% by weight, more preferably from 0.001 to 0.2% by weight, most preferably from 0.01 to 0.06% by weight, based in each case on monomer a). On increasing the amount of crosslinker b) the centrifuge retention capacity (CRC) decreases and the absorption under a pressure of 21.0 g/cm$^2$ (AUL) passes through a maximum.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane] dihydrochloride and 2,2'-azobis[2-(5-methyl-2-imidazolin-2-yl)propane] dihydrochloride, 2,2'-azobis(2-amidinopropane) dihydrochloride, 4,4'-azobis(4-cyanopentanoic acid), 4,4'-azobis(4-cyanopentanoic acid) sodium salt, 2,2'-azobis[2-methyl-N-(2-hydroxyethyl)propionamide], and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2- hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany). Of course it is also possible within the scope of the present invention to use the purified salts or acids of 2-hydroxy-2-sulfinatoacetic acid and 2-hydroxy-2-sulfonatoacetic acid— the latter being available as sodium salt under the trade name Blancolen® (Brüggemann Chemicals; Heilbronn; Germany).

The initiators are used in customary amounts, for example in amounts of from 0.001 to 5% by weight, preferably from 0.01 to 2% by weight, most preferably from 0.05 to 0.5% by weight, based on the monomers a).

Examples of ethylenically unsaturated monomers d) which are copolymerizable with the monomers a) are acrylamide, methacrylamide, hydroxyethyl acrylate, hydroxyethyl methacrylate, dimethylaminoethyl acrylate, dimethylaminoethyl methacrylate, dimethylaminopropyl acrylate and diethylaminopropyl methacrylate.

Useful water-soluble polymers e) include polyvinyl alcohol, modified polyvinyl alcohol comprising acidic side groups for example Poval® K (Kuraray Europe GmbH; Frankfurt; Germany), polyvinylpyrrolidone, starch, starch derivatives, modified cellulose such as methylcellulose, carboxymethylcellulose or hydroxyethylcellulose, gelatin, polyglycols or polyacrylic acids, polyesters and polyamides, polylactic acid, polyglycolic acid, co-polylactic-polyglycolic acid, polyvinylamine, polyallylamine, water soluble copolymers of acrylic acid and maleic acid available as Sokalan® (BASF SE; Ludwigshafen; Germany), preferably starch, starch derivatives and modified cellulose.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight.

The water content of the monomer solution is preferably less than 65% by weight, preferentially less than 62% by weight, more preferably less than 60% by weight, most preferably less than 58% by weight.

The monomer solution has, at 20° C., a dynamic viscosity of preferably from 0.002 to 0.02 Pas, more preferably from 0.004 to 0.015 Pas, most preferably from 0.005 to 0.01 Pas. The mean droplet diameter in the droplet generation rises with rising dynamic viscosity.

The monomer solution has, at 20° C., a density of preferably from 1 to 1.3 g/cm$^3$, more preferably from 1.05 to 1.25 g/cm$^3$, most preferably from 1.1 to 1.2 g/cm$^3$.

The monomer solution has, at 20° C., a surface tension of from 0.02 to 0.06 N/m, more preferably from 0.03 to 0.05 N/m, most preferably from 0.035 to 0.045 N/m. The mean droplet diameter in the droplet generation rises with rising surface tension—this is relevant if a dropletization polymerization process is used.

Polymerization

The monomer solution is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

Alternatively the water-absorbent polymer particles are produced by polymerizing droplets of the monomer in a surrounding heated gas phase, for example by using a system described in WO 2008/040715 A2, WO 2008/052971 A1, WO 2008/069639 A1 and WO 2008/086976 A1. The resulting water-absorbent polymer particles, especially have a roundness of at least 0.80.

The droplets are preferably generated by means of a droplet plate. A droplet plate is a plate having a multitude of bores, the liquid entering the bores from the top. The droplet plate or the liquid can be oscillated, which generates a chain of ideally monodisperse droplets at each bore on the underside of the droplet plate. In a preferred embodiment, the droplet plate is not agitated.

It is also possible to use two or more droplet plates with different bore diameters so that a range of desired particle sizes can be produced. It is preferable that each droplet plate carries only one bore diameter, however mixed bore diameters in one plate are also possible.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The Reynolds number based on the throughput per bore and the bore diameter is preferably less than 2000, preferentially less than 1600, more preferably less than 1400 and most preferably less than 1200.

The underside of the droplet plate has at least in part a contact angle preferably of at least 60°, more preferably at least 75° and most preferably at least 90° with regard to water.

The contact angle is a measure of the wetting behavior of a liquid, in particular water, with regard to a surface, and can be determined using conventional methods, for example in accordance with ASTM D 5725. A low contact angle denotes good wetting, and a high contact angle denotes poor wetting.

It is also possible for the droplet plate to consist of a material having a lower contact angle with regard to water, for example a steel having the German construction material code number of 1.4571, and be coated with a material having a larger contact angle with regard to water.

Useful coatings include for example fluorous polymers, such as perfluoroalkoxyethylene, poly-tetrafluoroethylene, ethylene-chlorotrifluoroethylene copolymers, ethylene-tetrafluoroethylene copolymers and fluorinated polyethylene.

The coatings can be applied to the substrate as a dispersion, in which case the solvent is subsequently evaporated off and the coating is heat treated. For polytetrafluoroethylene this is described for example in U.S. Pat. No. 3,243,321.

Further coating processes are to be found under the headword "Thin Films" in the electronic version of "Ullmann's Encyclopedia of Industrial Chemistry" (Updated Sixth Edition, 2000 Electronic Release).

The coatings can further be incorporated in a nickel layer in the course of a chemical nickelization.

It is the poor wettability of the droplet plate that leads to the production of monodisperse droplets of narrow droplet size distribution.

The droplet plate has preferably at least 5, more preferably at least 25, most preferably at least 50 and preferably up to 750, more preferably up to 500 bores, most preferably up to 250. The number of bores is determined mainly by geometrical and manufacturing constraints and can be adjusted to practical use conditions even outside the above given range. The diameter of the bores is adjusted to the desired droplet size.

The separation of the bores is usually from 5 to 50 mm, preferably from 6 to 40 mm, more preferably from 7 to 35 mm, most preferably from 8 to 30 mm. Smaller separations of the bores may cause agglomeration of the polymerizing droplets.

The diameter of the bores is preferably from 50 to 500 µm, more preferably from 100 to 300 µm, most preferably from 150 to 250 µm.

For optimizing the average particle diameter, droplet plates with different bore diameters can be used. The variation can be done by different bores on one plate or by using different plates, where each plate has a different bore diameter. The average particle size distribution can be monomodal, bimodal or multimodal. Most preferably it is monomodal or bimodal.

The temperature of the monomer solution as it passes through the bore is preferably from 5 to 80° C., more preferably from 10 to 70° C., most preferably from 30 to 60° C.

A gas flows through the reaction chamber. The carrier gas is conducted through the reaction chamber in co-current to the free-falling droplets of the monomer solution, i.e. from the top downward. After one pass, the gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The carrier gas may be composed of air. The oxygen content of the carrier gas is preferably from 0.1 to 15% by volume, more preferably from 1 to 10% by volume, most preferably from 2 to 7% by weight. In the scope of the present invention it is also possible to use a carrier gas which is free of oxygen.

As well as oxygen, the carrier gas preferably comprises nitrogen. The nitrogen content of the gas is preferably at least 80% by volume, more preferably at least 90% by volume, most preferably at least 95% by volume. Other possible carrier gases may be selected from carbon dioxide, argon, xenon, krypton, neon, helium, sulfurhexafluoride. Any mixture of carrier gases may be used. The carrier gas may also become loaded with water and/or acrylic acid vapors.

The gas velocity is preferably adjusted such that the flow in the reaction zone is directed, for example no convection currents opposed to the general flow direction are present, and is preferably from 0.1 to 2.5 m/s, more preferably from 0.3 to 1.5 m/s, even more preferably from 0.5 to 1.2 m/s, most preferably from 0.7 to 0.9 m/s.

The gas entrance temperature, i.e. the temperature with which the gas enters the reaction zone, is preferably from 160 to 200° C., more preferably from 165 to 195° C., even more preferably from 170 to 190° C., most preferably from 175 to 185° C.

The steam content of the gas that enters the reaction zone is preferably from 0.01 to 0.15 kg per kg dry gas, more preferably from 0.02 to 0.12 kg per kg dry gas, most preferably from 0.03 to 0.10 kg per kg dry gas.

The gas entrance temperature is controlled in such a way that the gas exit temperature, i.e. the temperature with which the gas leaves the reaction zone, is less than 150° C., preferably from 90 to 140° C., more preferably from 100 to 130° C., even more preferably from 105 to 125° C., most preferably from 110 to 120° C.

The steam content of the gas that leaves the reaction zone is preferably from 0.02 to 0.30 kg per kg dry gas, more from 0.04 to 0.28 kg per kg dry gas, most from 0.05 to 0.25 kg per kg dry gas.

The water-absorbent polymer particles can be divided into three categories: water-absorbent polymer particles of Type 1 are particles with one cavity, water-absorbent polymer particles of Type 2 are particles with more than one cavity, and water-absorbent polymer particles of Type 3 are solid particles with no visible cavity. Type 1 particles are represented by hollow-spheres, Type 2 particles are represented by spherical closed cell sponges, and Type 3 particles are represented by solid spheres. Type 2 or Type 3 particles or mixtures thereof with little or no Type 1 particles are preferred.

The morphology of the water-absorbent polymer particles can be controlled by the reaction conditions during polymerization. Water-absorbent polymer particles having a high amount of particles with one cavity (Type 1) can be prepared by using low gas velocities and high gas exit temperatures. Water-absorbent polymer particles having a high amount of particles with more than one cavity (Type 2) can be prepared by using high gas velocities and low gas exit temperatures.

Water-absorbent polymer particles having no cavity (Type 3) and water-absorbent polymer particles having more than one cavity (Type 2) show an improved mechanical stability compared with water-absorbent polymer particles having only one cavity (Type 1).

As a particular advantage round shaped particles have no edges that can easily be broken by processing stress in diaper production and during swelling in aqueous liquid there are no break-points on the surface that could lead to loss of mechanical strength.

The reaction can be carried out under elevated pressure or under reduced pressure, preferably from 1 to 100 mbar below ambient pressure, more preferably from 1.5 to 50 mbar below ambient pressure, most preferably from 2 to 10 mbar below ambient pressure.

The reaction off-gas, i.e. the gas leaving the reaction chamber, may be cooled in a heat exchanger. This condenses water and unconverted monomer a). The reaction off-gas can then be reheated at least partly and recycled into the reaction chamber as cycle gas. A portion of the reaction off-gas can be discharged and replaced by fresh gas, in which case water and unconverted monomers a) present in the reaction off-gas can be removed and recycled.

Particular preference is given to a thermally integrated system, i.e. a portion of the waste heat in the cooling of the off-gas is used to heat the cycle gas.

The reactors can be trace-heated. In this case, the trace heating is adjusted such that the wall temperature is at least 5° C. above the internal reactor temperature and condensation on the reactor walls is reliably prevented.

Thermal Posttreatment

The water-absorbent polymer particles obtained by dropletization optionally be thermal post-treated for adjusting the content of residual monomers to the desired value.

The residual monomers can be removed better at relatively high temperatures and relatively long residence times. What is important here is that the water-absorbent polymer particles are not too dry. In the case of excessively dry particles, the residual monomers decrease only insignificantly. Too high a water content increases the caking tendency of the water-absorbent polymer particles.

The thermal posttreatment can be done in a fluidized bed. In a preferred embodiment of the present invention an internal fluidized bed is used. An internal fluidized bed means that the product of the dropletization polymerization is accumulated in a fluidized bed below the reaction zone.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream in the fluidized bed is preferably from 0.3 to 2.5 m/s, more preferably from 0.4 to 2.0 m/s, most preferably from 0.5 to 1.5 m/s.

The pressure drop over the bottom of the internal fluidized bed is preferably from 1 to 100mbar, more preferably from 3 to 50mbar, most preferably from 5 to 25 mbar.

The moisture content of the water-absorbent polymer particles at the end of the thermal post-treatment is preferably from 1 to 20% by weight, more preferably from 2 to 15% by weight, even more preferably from 3 to 12% by weight, most preferably 5 to 8% by weight.

The temperature of the water-absorbent polymer particles during the thermal posttreatment is from 20 to 120° C., preferably from 40 to 100° C., more preferably from 50 to 95° C., even more preferably from 55 to 90° C., most preferably from 60 to 80° C.

The average residence time in the internal fluidized bed is from 10 to 300 minutes, preferably from 60 to 270 minutes, more preferably from 40 to 250 minutes, most preferably from 120 to 240 minutes.

The condition of the fluidized bed can be adjusted for reducing the amount of residual monomers of the water-absorbent polymers leaving the fluidized bed. The amount of residual monomers can be reduced to levels below 0.1% by weight by a thermal posttreatment using additional steam. The steam content of the gas is preferably from 0.005 to 0.25 kg per kg of dry gas, more preferably from 0.01 to 0.2 kg per kg of dry gas, most preferably from 0.02 to 0.15 kg per kg of dry gas.

By using additional steam the condition of the fluidized bed can be adjusted that the amount of residual monomers of the water-absorbent polymers leaving the fluidized bed is from 0.03 to 15% by weight, preferably from 0.05 to 12% by weight, more preferably from 0.1 to 10% by weight, even more preferably from 0.15 to 7.5% by weight most preferably from 0.2 to 5% by weight, even most preferably from 0.25 to 2.5% by weight.

It is preferred that the thermal posttreatment is completely or at least partially done in an external fluidized bed. The operating conditions of the external fluidized bed are within the scope for the internal fluidized bed as described above.

It is alternatively preferred that the thermal posttreatment is done in an external mixer with moving mixing tools, preferably horizontal mixers, such as screw mixers, disk mixers, screw belt mixers and paddle mixers. Suitable mixers are, for example, Becker shovel mixers (Gebr. Lödige Maschinenbau GmbH; Paderborn; Germany), Nara paddle mixers (NARA Machinery Europe; Frechen; Germany), Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; U.S.A.) and Ruberg continuous flow mixers (Gebrüder Ruberg GmbH & Co KG, Nieheim, Germany). Ruberg continuous flow mixers, Becker shovel mixers and Pflugschar® plowshare mixers are preferred.

The thermal posttreatment can be done in a discontinuous external mixer or a continuous external mixer.

The amount of gas to be used in the discontinuous external mixer is preferably from 0.01 to 5 Nm$^3$/h, more preferably from 0.05 to 2 Nm$^3$/h, most preferably from 0.1 to 0.5 Nm$^3$/h, based in each case on kg water-absorbent polymer particles.

The amount of gas to be used in the continuous external mixer is preferably from 0.01 to 5 Nm$^3$/h, more preferably from 0.05 to 2 Nm$^3$/h, most preferably from 0.1 to 0.5 Nm$^3$/h, based in each case on kg/h throughput of water-absorbent polymer particles.

The other constituents of the gas are preferably nitrogen, carbon dioxide, argon, xenon, krypton, neon, helium, air or air/nitrogen mixtures, more preferably nitrogen or air/nitrogen mixtures comprising less than 10% by volume of oxygen. Oxygen may cause discoloration.

The morphology of the water-absorbent polymer particles can also be controlled by the reaction conditions during thermal posttreatment. Water-absorbent polymer particles having a high amount of particles with one cavity (Type 1) can be prepared by using high product temperatures and short residence times. Water-absorbent polymer particles having a high amount of particles with more than one cavity (Type 2) can be prepared by using low product temperatures and long residence times.

Surface-Postcrosslinking

The water-absorbent polymer particles independent of their production process e.g. in a kneader or dropletization optionally can be surface-postcrosslinked to further adjust the properties of the fluid-absorbent particles, whereas according to the present invention the water-absorbent polymer particles are non-surface-postcrosslinked.

Surface-postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230. Also ethyleneoxide, aziridine, glycidol, oxetane and its derivatives may be used.

Polyvinylamine, polyamidoamines and polyvinylalcohole are examples of multifunctional polymeric surface-postcrosslinkers.

In addition, DE 40 20 780 C1 describes alkylene carbonates, DE 198 07 502 A1 describes 1,3-oxazolidin-2-one and its derivatives such as 2-hydroxyethyl-1,3-oxazolidin-2-one, DE 198 07 992 C1 describes bis- and poly-1,3-oxazolidin-2-ones, EP 0 999 238 A1 describes bis- and poly-1,3-oxazolidines, DE 198 54 573 A1 describes 2-oxotetrahydro-1,3-oxazine and its derivatives, DE 198 54 574 A1 describes N-acyl-1,3-oxazolidin-2-ones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable surface-postcrosslinkers.

In addition, it is also possible to use surface-postcrosslinkers which comprise additional polymerizable ethylenically unsaturated groups, as described in DE 37 13 601 A1.

It is also possible to use any suitable mixture of surface-postcrosslinkers.

The temperature during the thermal surface-postcrosslinking is in the range from 100 to 180° C.

Coating

To improve the properties, the water-absorbent polymer particles can be coated and/or optionally moistened.

The internal fluidized bed, the external fluidized bed and/or the external mixer used for the thermal posttreatment and/or a separate coater (mixer) can be used for coating of the water-absorbent polymer particles. Further, the cooler and/or a separate coater (mixer) can be used for coating/moistening of the surface-postcrosslinked water-absorbent polymer particles. Suitable coatings for controlling the acquisition behavior and the permeability (SFC or GBP) are, for example, inorganic inert substances, such as water-insoluble metal salts, organic polymers, cationic polymers, anionic polymers and polyvalent metal cations.

Suitable coatings for improving the color stability are, for example reducing agents, chelating agents and anti-oxidants. Suitable coatings for dust binding are, for example, polyols. Suitable coatings against the undesired caking tendency of the polymer particles are, for example, fumed silica, such as Aerosil® 200, and surfactants, such as Span® 20 and Plantacare® 818 UP. Preferred coatings are aluminium dihydroxy monoacetate, aluminium sulfate, aluminium lactate, aluminium 3-hydroxypropionate, zirconium acetate, citric acid or its water soluble salts, di- and monophosphoric acid or their water soluble salts, Blancolen®, Brüggolite® FF7, Cublen®, Span® 20 and Plantacare® 818 UP.

But as the water-absorbent polymer particles according to the invention are non-surface post-crosslinked they are usually also not coated.

But especially in case of problems with colour stability and/or dust binding it could be preferred also to coat the non-surface postcrosslinked water-absorbent polymer particles.

Agglomeration

The water-absorbent polymer particles can further selectively be agglomerated. The agglomeration can take place after the polymerization, the thermal postreatment, the thermal surface-post-crosslinking or the coating.

Useful agglomeration assistants include water and water-miscible organic solvents, such as alcohols, tetrahydrofuran and acetone; water-soluble polymers can be used in addition.

For agglomeration a solution comprising the agglomeration assistant is sprayed onto the water-absorbing polymeric particles. The spraying with the solution can, for example, be carried out in mixers having moving mixing implements, such as screw mixers, paddle mixers, disk mixers, plowshare mixers and shovel mixers. Useful mixers include for example Lödige® mixers, Bepex® mixers, Nauta® mixers, Processall® mixers and Schugi® mixers. Vertical mixers are preferred. Fluidized bed apparatuses are particularly preferred.

The surfactants and/or the inorganic inert substances can be used to avoid sticking or caking during this process step under humid atmospheric conditions. Preferred surfactants are non-ionic and amphoteric surfactants. Preferred inorganic inert substances are precipitated silicas and fumed silicas in form of powder or dispersion.

The amount of total liquid used for preparing the solutions/dispersions is typically from 0.01% to 25% by weight, preferably from 0.5% to 12% by weight, more preferably from 2% to 7% by weight, most preferably from 3% to 6% by weight, in respect to the weight amount of water-absorbent polymer particles to be processed.

As the centrifuge retention capacity (CRC) is the maximum water retention capacity of the water-absorbent polymer particles it is of interest to maximize this parameter.

The water-absorbent polymer particles suitable for the inventive fluid-absorbent article have a centrifuge retention capacity of at least 35 g/g, preferably 40 g/g.

The fluid-absorbent polymer particles according to one embodiment of the present invention have a centrifuge retention capacity (CRC) of typically at least 35 g/g, preferably at least 40 g/g, more preferably at least 45 g/g, most preferably at least 50 g/g and usually not above 100 g/g. The water-absorbent polymer particles suitable further having a level of extractable constituents of less than 20% by weight, preferably less than 15%, preferentially less than 10%, more preferably less than 8%, even more preferably less than 5% and usually not above 3%.

The absorbency under no load (AUNL) of the water-absorbent polymer particles according to one embodiment of the present invention is at least 35 g/g, preferably at least 40 g/g, preferentially at least 45 g/g, more preferably at least 50 g/g, even more preferably at least 55 g/g and usually not above 100 g/g.

The absorbency under high load (AUHL) of water-absorbent polymer particles useful in the invention is at least 5 g/g but preferably less than 20 g/g, more preferably less than 15 g/g, preferentially less than 10 g/g even more preferably less than 8 g/g.

Water-absorbent polymer particles according to an embodiment of the present invention have a saline flow conductivity (SFC) of less than $5 \times 10^{-7}$ cm$^3$s/g, preferably less than $4 \times 10^{-7}$ cm$^3$s/g, preferentially less than $3 \times 10^{-7}$ cm$^3$s/g, more preferably less than $2 \times 10^{-7}$ cm$^3$s/g, even more preferably less than $1 \times 10^{-7}$ cm$^3$s/g and usually not above $0 \times 10^{-7}$ cm$^3$s/g.

Water-absorbent polymer particles according to an embodiment of the invention have a centrifuge retention capacity of at least 35 g/g, an absorbency under no load (AUNL) of at least 35 g/g, an absorbency under high load (AUHL) of at least 5 g/g and have a saline flow conductivity (SFC) of less than $5 \times 10^{-7}$ cm$^3$s/g.

According to another embodiment of the invention water-absorbent polymer particles having a centrifuge retention capacity (CRC) of at least 37 g/g, an absorbency under no load (AUNL) of at least 40 g/g, an absorbency under high load (AUHL) of at least 6 g/g and a saline flow conductivity (SFC) of less than $3\times10^{-7}$ cm$^3$s/g.

Preferred water-absorbent polymer particles according to an embodiment of the invention have a centrifuge retention capacity of at least 35 g/g, an absorbency under no load (AUNL) of at least 35 g/g, an absorbency under high load (AUHL) of less than 15 g/g and have a saline flow conductivity (SFC) of less than $5\times10^{-7}$ cm$^3$s/g.

More preferred water-absorbent polymer particles according to an embodiment of the invention have a centrifuge retention capacity of at least 40 g/g, an absorbency under no load (AUNL) of at least 40 g/g, an absorbency under high load (AUHL) of less than 15 g/g and have a saline flow conductivity (SFC) of less than $5\times10^{-7}$ cm$^3$s/g.

Even more preferred water-absorbent polymer particles having a centrifuge retention capacity (CRC) of at least 37 g/g, an absorbency under no load (AUNL) of at least 40 g/g, an absorbency under high load (AUHL) of less than 10 g/g and a saline flow conductivity (SFC) of less than $3\times10^{-7}$ cm$^3$s/g.

According to one embodiment the water-absorbing particles useful for the present invention have a mean sphericity from 0.80 to 0.95, preferably from 0.82 to 0.93, more preferably from 0.84 to 0.91, most preferably from 0.85 to 0.90. The sphericity (SPHT) or roundness is defined as $$SPHT = \frac{4\pi A}{U^2},$$

where A is the cross-sectional area and U is the cross-sectional circumference of the polymer particles. The mean sphericity is the volume-average sphericity.

The mean sphericity can be determined, for example, with the Camsizer® image analysis system (Retsch Technolgy GmbH; Haan; Germany) or with the PartAn® 3001 L Particle Analysator (Microtrac Europe GmbH; Meerbusch; Germany).

Suitable water-absorbent polymer particles have a bulk density preferably from 0.6 to 1 g/cm$^3$, more preferably from 0.65 to 0.9 g/cm$^3$, most preferably from 0.68 to 0.8 g/cm$^3$.

Whereas it is preferred that water-absorbent polymer particles with a sphericity of less than 0.80 having a bulk density of from 0.6 to 0.75 g/cm$^3$, preferably from 0.62 to 0.68 g/cm$^3$.

Whereas it is preferred that water-absorbent polymer particles with a sphericity of at least 0.80 having a bulk density of at least 0.75.

The useful water-absorbent particles having a particle size distribution (PSD) of 150 µm to 850 µm, preferably of 150 µm to 700 µm, more preferably of 150 µm to 600µm, most preferably 150 µm to 400 µm.

C. Fluid-Absorbent Articles

The fluid-absorbent article comprises
(A) an upper liquid-pervious layer
(B) a lower liquid-impervious layer
(C) at least 60% by weight non-surface postcrosslinked fluid-absorbent polymer particles and not more than 40% by weight of cellulose based fibers, preferably at least 65% by weight non-surface postcrosslinked fluid-absorbent polymer particles and not more than 35% by weight of cellulose based fibers, more preferably at least 70% by weight non-surface postcrosslinked fluid-absorbent polymer particles and not more than 30% by weight of cellulose based fibers, most preferably at least 80% by weight non-surface postcrosslinked fluid-absorbent polymer particles and not more than 20% by weight of cellulose based fibers, even more preferably at least 90% by weight non-surface postcrosslinked fluid-absorbent polymer particles and not more than 10% by weight of cellulose based fibers, even more preferably 100% by weight non-surface postcrosslinked fluid-absorbent polymer particles and 0% by weight of cellulose based fibers based on the sum of fluid-absorbent polymer particles and cellulose based fibres, and
(D) an acquisition-distribution layer(ADL) between (A) and (C) comprising at least 90% by weight of synthetic fibers and not more than 10% by weight of cellulose based fibers, based on the sum of synthetic fibers and cellulose based fibers, the ADL having a basis weight of at least 70 gsm, preferably at least 80 gsm, more preferably at least 90 gsm, most preferably at least 100 gsm, usually not above 180 gsm; and
(E) an optional tissue layer disposed immediately above and/or below (C) or wrapped fully or partially around (C); and
(F) other optional components.

Fluid-absorbent articles are understood to mean, for example, incontinence pads and incontinence briefs for adults or diapers and training pants for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

The acquisition-distribution layer acts as transport and distribution layer of the discharged body fluids and is typically optimized to affect efficient liquid distribution with the underlying fluid-absorbent core. Hence, for quick temporary liquid retention it provides the necessary void space while its area coverage of the underlying fluid-absorbent core must affect the necessary liquid distribution and is adopted to the ability of the fluid-absorbent core to quickly dewater the acquisition-distribution layer.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core, acting as transport and distribution layer of the discharged body fluids. These individual elements are combined such that the resultant fluid-absorbent article meets overall criteria such as flexibility, water vapour breathability, dryness, wearing comfort and protection on the user facing side, and concerning liquid retention, rewet and prevention of wet through on the garment side. The specific combination of these layers provides a fluid-absorbent article delivering both high protection levels as well as high comfort to the consumer.

Designs for fluid-absorbent articles and methods to make them are for example described in the following publications and literature cited therein and are expressly incorporated into the present invention: EP 2 301 499 A1, EP 2 314 264 A1, EP 2 387 981 A1, EP 2 486 901 A1, EP 2 524 679 A1, EP 2 524 679 A1, EP 2 524 680 A1, EP 2 565 031 A1, U.S. Pat. No. 6,972,011, US 2011/0162989, US 2011/0270204, WO 2010/004894 A1, WO 2010/004895 A1, WO 2010/076857 A1, WO 2010/082373 A1, WO 2010/118409 A1, WO 2010/133529 A2, WO 2010/143635 A1, WO 2011/084981 A1, WO 2011/086841 A1, WO 2011/086842 A1, WO 2011/086843 A1, WO 2011/086844 A1, WO 2011/117997 A1, WO 2011/136087 A1, WO 2012/048879 A1, WO 2012/052173 A1 and WO 2012/052172 A1, U.S. Pat. No. 7,378,568 B2.

Figure 7:
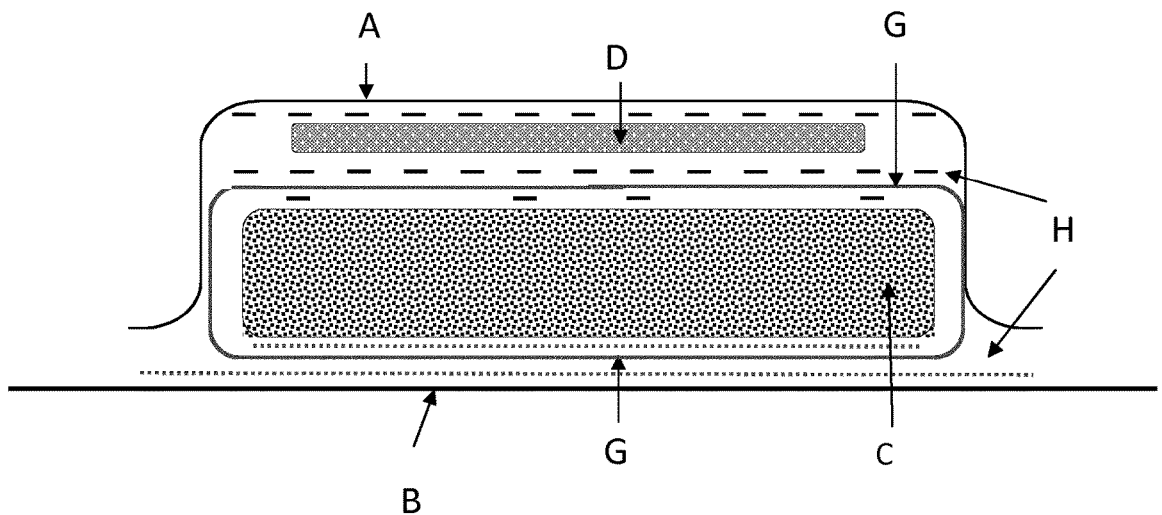

FIG. 7 shows a cross section of an example of an absorbent article according to the invention.

An absorbent article according to the invention preferably comprise as shown in FIG. 7 an upper liquid-pervious layer (A), a lower liquid-impervious layer (B) at least one fluid absorbent core (C) between (A) and (B); and an acquisition-distribution layer (D) between (A) and (C), an optional tissue layer (G) disposed immediately above and/or below (C) or wrapped fully or partially around (C). These layers are preferably joined to each e.g. by addition of adhesives or by mechanical, thermal or ultrasonic bonding or combinations thereof (H).

Liquid-Pervious Layer (A)

The liquid-pervious layer (A) is the layer which is in direct contact with the skin. Thus, the liquid-pervious layer is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thickness. The principle function of the liquid-pervious layer is the acquisition and transport of body fluids from the wearer towards the fluid-absorbent core. Typically liquid-pervious layers are formed from any materials known in the art such as nonwoven material, films or combinations thereof. Suitable liquid-pervious layers (A) consist of customary synthetic or semisynthetic fibers or bicomponent fibers or films of polyester, polyolefins, rayon or natural fibers or any combinations thereof. In the case of nonwoven materials, the fibers should generally be bound by binders such as poly-acrylates. Additionally the liquid-pervious layer may contain elastic compositions thus showing elastic characteristics allowing to be stretched in one or two directions.

Suitable synthetic fibers are made from polyvinyl chloride, polyvinyl fluoride, polytetrafluorethylene, polyvinylidene chloride, polyacrylics, polyvinyl acetate, polyethylvinyl acetate, non-soluble or soluble polyvinyl alcohol, polyolefins such as polyethylene, polypropylene, polyamides, polyesters, polyurethanes, polystyrenes and the like.

Examples for films are apertured formed thermoplastic films, apertured plastic films, hydro-formed thermoplastic films, reticulated thermoplastic films, porous foams, reticulated foams, and thermoplastic scrims.

Examples of suitable modified or unmodified natural fibers include cotton, bagasse, kemp, flax, silk, wool, wood pulp, chemically modified wood pulp, jute, rayon, ethyl cellulose, and cellulose acetate.

Suitable wood pulp fibers can be obtained by chemical processes such as the Kraft and sulfite processes, as well as from mechanical processes, such as ground wood, refiner mechanical, thermo-mechanical, chemi-mechanical and chemi-thermo-mechanical pulp processes. Further, recycled wood pulp fibers, bleached, unbleached, elementally chlorine free (ECF) or total chlorine free (TCF) wood pulp fibers can be used.

The fibrous material may comprise only natural fibers or synthetic fibers or any combination thereof. Preferred materials are polyester, rayon and blends thereof, polyethylene, and polypropylene.

The fibrous material as a component of the fluid-absorbent compositions may be hydrophilic, hydrophobic or can be a combination of both hydrophilic and hydrophobic fibers. The definition of hydrophilic is given in the section "definitions" in the chapter above. The selection of the ratio hydrophilic/hydrophobic and accordingly the amount of hydrophilic and hydrophobic fibers within fluid-absorbent composition will depend upon fluid handling properties and the amount of water-absorbent polymer particles of the resulting fluid-absorbent composition. Such, the use of hydrophobic fibers is preferred if the fluid-absorbent composition is adjacent to the wearer of the fluid-absorbent article, that is to be used to replace partially or completely the upper liquid-pervious layer, preferably formed from hydrophobic nonwoven materials. Hydrophobic fibers can also be member of the lower breathable, but fluid-impervious layer, acting there as a fluid-impervious barrier.

Examples for hydrophilic fibers are cellulosic fibers, modified cellulosic fibers, rayon, polyester fibers such as polyethylen terephthalate, hydrophilic nylon and the like. Hydrophilic fibers can also be obtained from hydrophobic fibers which are hydrophilized by e. g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper-layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of raising the temperature in the presence of low-melting polymers. Examples for thermal bonding processes are spunbonding, through-air bonding and resin bonding.

Preferred means of increasing the integrity are thermal bonding, spunbonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulosic fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a monocomponent fiber. Alternatively, they can be made from more than one polymer, e.g., bi-component or multicomponent fibers. The term "bicomponent fibers" refers to thermoplastic fibers that comprise a core fiber made from a different fiber material than the shell. Typically, both fiber materials have different melting points, wherein generally the sheath melts at lower temperatures. Bi-component fibers can be concentric or eccentric depending whether the sheath has a thickness that is even or uneven through the cross-sectional area of the bi-component fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between about 75° C. and 175° C. The typical length of thermoplastic fibers is from about 0.4 to 6 cm, preferably from about 0.5 to 1 cm. The diameter of thermoplastic fibers is defined in terms of either denier (grams per 9000 meters) or dtex (grams per 10 000 meters). Typical thermoplastic fibers have a dtex in the range from about 1.2 to 20, preferably from about 1.4 to 10.

A further mean of increasing the integrity of the fluid-absorbent composition is the spunbonding technology. The nature of the production of fibrous layers by means of spunbonding is based on the direct spinning of polymeric granulates into continuous filaments and subsequently manufacturing the fibrous layer.

Spunbond fabrics are produced by depositing extruded, spun fibers onto a moving belt in a uniform random manner followed by thermal bonding the fibers. The fibers are separated during the web laying process by air jets. Fiber bonds are generated by applying heated rolls or hot needles to partially melt the polymer and fuse the fibers together. Since molecular orientation increases the melting point, fibers that are not highly drawn can be used as thermal binding fibers. Polyethylene or random ethylene/propylene copolymers are used as low melting bonding sites.

Besides spunbonding, the technology of resin bonding also belongs to thermal bonding subjects. Using this technology to generate bonding sites, specific adhesives, based on e.g. epoxy, polyurethane and acrylic are added to the fibrous material and the resulting matrix is thermically treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thickness between a hot roll calendered product and one that has been though-air bonded without compression. Even after cold calendering, this product is softer, more flexible and more extensible than area-bond hot-calendered material.

Spunlacing ("hydroentanglement") is a further method of increasing the integrity of a web. The formed web of loose fibers (usually air-laid or wet-laid) is first compacted and prewetted to eliminate air pockets. The technology of spunlacing uses multiple rows of fine high-speed jets of water to strike the web on a porous belt or moving perforated or patterned screen so that the fibers knot about one another. The water pressure generally increases from the first to the last injectors. Pressures as high as 150 bar are used to direct the water jets onto the web. This pressure is sufficient for most of the nonwoven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace nonwoven.

In newest researches benefits are found in some structural features of the resulting liquid-pervious layers.

Typically liquid-pervious layers (A) extend partially or wholly across the fluid-absorbent structure and can extend into and/or form part of all the preferred sideflaps, side wrapping elements, wings and ears.

Liquid-Impervious Layer (B)

The liquid-impervious layer (B) prevents the exudates absorbed and retained by the fluid-absorbent core from wetting articles which are in contact with the fluid-absorbent article, as for example bedsheets, pants, pyjamas and undergarments. The liquid-impervious layer (B) may thus comprise a woven or a nonwoven material, polymeric films such as thermoplastic film of polyethylene or polypropylene, or composite materials such as film-coated nonwoven material.

Suitable liquid-impervious layers include nonwoven, plastics and/or laminates of plastic and nonwoven. Both, the plastics and/or laminates of plastic and nonwoven may appropriately be breathable, that is, the liquid-impervious layer (B) can permit vapors to escape from the fluid-absorbent material. Thus the liquid-impervious layer has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polyvinylalcohol as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spunbonded nonwoven layer made from synthetic fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious layers are permeable for vapor. Preferably the liquid-impervious layer is constructed from vapor permeable material showing a water vapor transmission rate (WVTR) of at least about 100 gsm per 24 hours, preferably at least about 250 gsm per 24 hours and most preferred at least about 500 gsm per 24 hours.

Preferably the liquid-impervious layer (B) is made of nonwoven comprising hydrophobic materials, e.g. synthetic fibers or a liquid-impervious polymeric film comprising plastics e.g. polyethylene. The thickness of the liquid-impervious layer is preferably 15 to 30 µm.

Further, the liquid-impervious layer (B) is preferably made of a laminate of nonwoven and plastics comprising a nonwoven having a density of 12 to 15 gsm and a polyethylene layer having a thickness of about 10 to 20 µm.

The typically liquid-impervious layer (B) extends partially or wholly across the fluid-absorbent structure and can extend into and/or form part of all the preferred sideflaps, side wrapping elements, wings and ears.

Fluid-Absorbent Core (C)

The fluid-absorbent core (C) is disposed between the upper liquid-pervious layer (A) and the lower liquid-impervious layer (B). Suitable fluid-absorbent cores (C) may be selected from any of the fluid-absorbent core-systems known in the art provided that requirements such as vapor permeability, flexibility and thickness are met. Suitable fluid-absorbent cores refer to any fluid-absorbent composition whose primary function is to acquire, transport, distribute, absorb, store and retain discharged body fluids.

The top view area of the fluid-absorbent core (C) is preferably at least 200 $cm^2$, more preferably at least 250 $cm^2$, most preferably at least 300 $cm^2$. The top view area is the part of the core that is face-to-face to the upper liquid-pervious layer.

According to the present invention the fluid-absorbent core can include the following components:
1. an optional core cover
2. a fluid storage layer
3. an optional dusting layer 1. Optional Core Cover In order to increase the integrity of the fluid-absorbent core, the core is provided with a cover. This cover may be at the top and/or at the bottom of the fluid-absorbent core with bonding at lateral juncture and/or bonding at the distal juncture by hot-melt, ultrasonic bonding, thermal bonding or combination of bonding techniques know to persons skilled in the art. Further, this cover may include the whole fluid-absorbent core with a unitary sheet of material and thus function as a wrap. Wrapping is possible as a full wrap, a partial wrap or as a C-Wrap.

The material of the core cover may comprise any known type of substrate, including webs, garments, textiles, films, tissues and laminates of two or more substrates or webs. The core cover material may comprise natural fibers, such as cellulose, cotton, flax, linen, hemp, wool, silk, fur, hair and naturally occurring mineral fibers. The core cover material may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the core cover comprises synthetic fibers or tissue.

The fibers may be mono- or multicomponent. Multicomponent fibers may comprise a homopolymer, a copolymer or blends thereof.

2. Fluid-Storage Layer

The fluid-absorbent compositions included in the fluid-absorbent core comprise at least 60% by weight water-absorbent polymer particles and at maximum 40% by weight of fibrous material, based on the sum of fluid-absorbent polymer particles and fibrous material.

Fibers useful in the present invention include natural fibers and synthetic fibers. Examples of suitable modified or unmodified natural fibers are given in the chapter "Liquid-pervious Layer (A)" above. From those, wood pulp fibers are preferred.

Examples of suitable synthetic fibers are given in the chapter "Liquid-pervious Layer (A)" above. The fibrous material may comprise only natural fibers or synthetic fibers or any combination thereof.

The fibrous material as a component of the fluid-absorbent compositions may be hydrophilic, hydrophobic or can be a combination of both hydrophilic and hydrophobic fibers.

Generally for the use in a fluid-absorbent core, which is the embedded between the upper layer (A) and/or the ADL (D) respectively and the lower layer (B), hydrophilic fibers are preferred. This is especially the case for fluid-absorbent compositions that are desired to quickly acquire, transfer and distribute discharged body fluids to other regions of the fluid-absorbent composition or fluid-absorbent core. The use of hydrophilic fibers is especially preferred for fluid-absorbent compositions comprising water-absorbent polymer particles.

Examples for hydrophilic fibers are given in the chapter "Liquid-pervious Layer (A)" above.

The fibrous material of the fluid-absorbent core may be uniformly mixed to generate a homogenous or in-homogenous fluid-absorbent core. Alternatively the fibrous material may be concentrated or laid in separate layers optionally comprising water-absorbent polymer material. Suitable storage layers of the fluid-absorbent core comprising homogenous mixtures of fibrous materials comprising water-absorbent polymer material. Suitable storage layers of the fluid-absorbent core including a layered core-system comprise homogenous mixtures of fibrous materials and comprise water-absorbent polymer material, whereby each of the layers may be built from any fibrous material by means known in the art. The sequence of the layers may be directed such that a desired fluid acquisition, distribution and transfer results, depending on the amount and distribution of the inserted fluid-absorbent material, e.g. water-absorbent polymer particles.

Suitable fluid-absorbent cores comprise fibrous material and fluid-absorbent material. Suitable fibrous material are as described in the chapter "Liquid-pervious Layer (A)" above.

Suitable fluid-absorbent cores are also manufactured from loose fibrous materials by adding water-absorbent particles.

In the process of manufacturing the fluid-absorbent core, water-absorbent polymer particles are brought together with structure forming compounds such as fibrous matrices. Thus, the water-absorbent polymer particles may be added during the process of forming the fluid-absorbent core from loose fibers. The fluid-absorbent core may be formed by mixing water-absorbent polymer particles with fibrous materials of the matrix at the same time or adding one component to the mixture of two or more other components either at the same time or by continuously adding.

Suitable fluid-absorbent cores including mixtures of water-absorbent polymer particles and fibrous material building matrices for the incorporation of the fluid-absorbent material. Such mixtures can be formed homogenously, that is all components are mixed together to get a homogenous structure. The amount of the fluid-absorbent materials may be uniform throughout the fluid-absorbent core, or may vary, e.g. between the central region and the distal region to give a profiled core concerning the concentration of fluid-absorbent material.

Techniques of application of the water-absorbent polymer materials into the absorbent core are known to persons skilled in the art and may be volumetric, loss-in-weight or gravimetric. Known techniques include the application by vibrating systems, single and multiple auger systems, dosing roll, weigh belt, fluid bed volumetric systems and gravitational sprinkle and/or spray systems. Further techniques of insertion are falling dosage systems consensus and contradictory pneumatic application or vacuum printing method of applying the fluid absorbent polymer materials.

Preferably drum-forming techniques are used where the fluid-absorbent core is formed in cavities of a drum rotating about a horizontal axis and being fed at a point on its periphery with a flow of water-absorbent polymer particles and/or fluid-absorbent fibers and fibrous material. The cylindrical surface of the drum on which the fluid-absorbent core is formed is surmounted by a hood, into which said flow is fed pneumatically from the top, bottom or tangentially. The inside of the hood may also contain the outlet of a feed duct, from which discrete quantities of additional water-absorbent polymer particles are dispensed by intermittently operating valve means under pressure. However, using prior art drum-forming techniques it is not possible to obtain uniform distribution of discrete quantities of water-absorbent polymer particles. Thus, in order to get pro-filed structures having different concentrations of water-absorbent polymer particles in discrete areas, it is preferred to use the technique written in WO 2010103453 in detail. Using this unit for the production of absorbent cores, by which a defined proportion of water-absorbent polymer particles are dispensed intermittently and controllably by adjustable elements controlling position and speed of application, it is possible to apply discrete quantities of water-absorbent polymer particles to a circumscribed area of precise geometrical shape.

Suitable fluid-absorbent cores may also include layers, which are formed by the process of manufacturing the fluid-absorbent article. The layered structure may be formed by subsequently generating the different layers in z-direction.

Typically the fluid-absorbent core may contain a single type of water-absorbent polymer particles or may contain water-absorbent polymer particles derived from different types of water-absorbent polymer material.

In case different types of water-absorbent polymer material used, the at least two different water-absorbent polymer materials may be mixed in the same or different quantities or the materials also be placed each in different layers within the absorbent core. Whereas each layer may contain the same amount of water-absorbent polymer material or the amount may differ.

Furthermore it is preferred that the water-absorbent polymer particles are placed within the core in discrete regions even without chambers, e.g. supported by at least an adhesive. Suitable preformed layers are processed as e.g. air-laid, wet-laid, laminate or composite structure.

It is particularly preferred according to the present invention that the fluid-absorbent core of the inventive fluid-absorbent article comprises at least 60% by weight of water-absorbent polymer particles, more preferred at least 65% by weight of water-absorbent polymer particles, most preferred at least 70% by weight of water-absorbent polymer particles, particularly preferred at least 90% by weight of water-absorbent polymer particles.

It is preferred that the fluid-absorbent core comprises at maximum 40% by weight fibrous material, more preferred at maximum 30%, most preferred at maximum 10% by weight fibrous material.

The quantity of water-absorbent polymer particles within the fluid-absorbent core is typically up to about 14 g, occasionally up to 16 g in the case of maxi-diapers, and generally in the case of incontinence products up to about 30 g, occasionally up to more than 45 g.

The fluid-absorbent core may comprise additional additives typically present in fluid-absorbent articles known in the art. Exemplary additives are fibers for reinforcing and stabilizing the fluid-absorbent core. Preferably polyethylene is used for reinforcing the fluid-absorbent core.

Further suitable stabilizer for reinforcing the fluid-absorbent core are materials acting as binder. In varying the kind of binder material or the amount of binder used in different regions of the fluid-absorbent core it is possible to get a profiled stabilization. For example, different binder materials exhibiting different melting temperatures may be used in regions of the fluid-absorbent core, e.g. the lower melting one in the central region of the core, and the higher melting in the distal regions. Suitable binder materials may be adhesive or non-adhesive fibers, continuously or discontinuously extruded fibers, bi-component staple fibers, non-elastomeric fibers and sprayed liquid binder or any combination of these binder materials.

Further, thermoplastic compositions usually are added to increase the integrity of the core layer. Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefin or styrene block copolymer and mixture of waxes.

Suitable thermoplastic polymers are styrenic block copolymers including A-B-A triblock segments, A-B diblock segments and $(A-B)_n$ radial block copolymer segments. The letter A designs non-elastomeric polymer segments, e.g. polystyrene, and B stands for unsaturated conjugated diene or their (partly) hydrogenated form. Preferably B comprises isoprene, butadiene, ethylene/butylene (hydrogenated butadiene), ethylene/propylene (hydrogenated isoprene) and mixtures thereof.

Other suitable thermoplastic polymers are amorphous polyolefins, amorphous polyalphaolefins and metallocene polyolefins.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid.

Suitable odor control additives are further antimicrobial agents such as quaternary ammonium, phenolic, amide and nitro compounds and mixtures thereof; bactericides such as silver salts, zinc salts, cetylpyridinium chloride and/or triclosan as well as surfactants having an HLB value of less than 12.

Suitable odor control additives are further compounds with anhydride groups such as maleic-, itaconic-, polymaleic- or polyitaconic anhydride, copolymers of maleic acid with $C_2$-$C_8$ olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or co-polymers of $C_3$-$C_5$ mono-unsaturated carboxylic acids.

Suitable odor control additives are further perfumes such as allyl caproate, allyl cyclohexaneacetate, allyl cyclohexanepropionate, allyl heptanoate, amyl acetate, amyl propionate, anethol, anixic aldehyde, anisole, benzaldehyde, benzyl acetete, benzyl acetone, benzyl alcohole, benzyl butyrate, benzyl formate, camphene, camphor gum, laevocarveol, cinnamyl formate, cis-jasmone, citral, citronellol and its derivatives, cuminic alcohol and its derivatives, cyclal C, dimethyl benzyl carbinol and its derivatives, dimethyl octanol and its derivatives, eucalyptol, geranyl derivatives, lavandulyl acetete, ligustral, d-limonene, linalool, linalyl derivatives, menthone and its derivatives, myrcene and its derivatives, neral, nerol, p-cresol, p-cymene, orange terpenes, alpha-ponene, 4-terpineol, thymol etc.

Masking agents are also used as odor control additives. Masking agents are in solid wall material encapsulated perfumes. Preferably, the wall material comprises a fluid-soluble cellular matrix which is used for time-delay release of the perfume ingredient.

Further suitable odor control additives are transition metals such as Cu, Ag, Zn; enzymes such as urease-inhibitors, starch, pH buffering material, chitin, green tea plant extracts, ion exchange resin, carbonate, bicarbonate, phosphate, sulfate or mixtures thereof.

Preferred odor control additives are green tea plant extracts, silica, zeolite, carbon, starch, chelating agent, pH buffering material, chitin, kieselguhr, clay, ion exchange resin, carbonate, bicarbonate, phosphate, sulfate, masking agent or mixtures thereof. Suitable concentrations of odor control additives are from about 0.5 to about 300 gsm.

Newest developments propose the addition of wetness indication additives. Besides electrical monitoring the wetness in the fluid-absorbent article, wetness indication additives comprising a hot melt adhesive with a wetness indicator are known. The wetness indication additive changes the colour from yellow to a relatively dark and deep blue. This colour change is readily perceivable through the liquid-impervious outer material of the fluid-absorbent article. Existing wetness indication is also achieved via application of water soluble ink patterned on the backsheet which disappears when wet.

Suitable wetness indication additives comprising a mixture of sorbitan monooleate and polyethoxylated hydrogenated castor oil. Preferably, the amount of the wetness indication additive is in the range of about 0.0001 to 2% by weight related to the weight of the fluid-absorbent core.

The basis weight of the fluid-absorbent core is in the range of 300 to 1200 gsm, preferably 450 to 1000 gsm. The density of the fluid-absorbent core is in the range of 0.1 to 0.25 g/cm$^3$. The thickness of the fluid-absorbent core is in the case of diapers in the range of 1 to 5 mm, preferably 1.5 to 3 mm, in the case of incontinence products in the range of 3 to 15 mm.

3. Optional Dusting Layer

An optional component for inclusion into the absorbent core is a dusting layer adjacent to. The dusting layer is a fibrous layer and may be placed on the top and/or the bottom of the absorbent core. Typically, the dusting layer is underlying the storage layer. This underlying layer is referred to as a dusting layer, since it serves as carrier for deposited water-absorbent polymer particles during the manufacturing process of the fluid-absorbent core. If the water-absorbent polymer material is in the form of macrostructures, films or flakes, the insertion of a dusting layer is not necessary. In the case of water-absorbent polymer particles derived from dropletization polymerization, the particles have a smooth surface with no edges. Also in this case, the addition of a dusting layer to the fluid-absorbent core is not necessary. On the other side, as a great advantage the dusting layer provides some additional fluid-handling properties such as wicking performance and may offer reduced incidence of pin-holing and or pock marking of the liquid impervious layer (B).

Preferably, the dusting layer is a fibrous layer comprising fluff (cellulose fibers).

Acquisition-Distribution Layer (D)

The acquisition-distribution layer (D) is located between the upper layer (A) and the fluid-absorbent core (C) and is preferably constructed to efficiently acquire discharged body fluids and to transfer and distribute them to other regions of the fluid-absorbent composition or to other layers, where the body fluids are immobilized and stored. Thus, the upper layer transfers the discharged liquid to the acquisition-distribution layer (D) for distributing it to the fluid-absorbent core.

In case of diapers the length of the acquisition-distribution layer is in its longitudinal direction shorter than the fluid-absorbing core. The length of the acquisition-distribution layer is in its longitudinal direction typically at least 30%, preferred at least 40%, more preferred at least 60% of the length of the fluid-absorbent core.

Typically the acquisition-distribution layer is not centered on the fluid-absorbing core. It is important that according to the invention the insult point or pee-point, the point where the body-fluid is/or is expected to be insulted by the wearer of the respective fluid-absorbent article is within the ADL.

Fluid-absorbent articles according to the invention comprise acquisition-distribution layers with a basis weight of 70 gsm, preferably of 80 gsm, more preferably of 90 gsm, most preferably at least 100 gsm but usually not higher than 180 gsm. An ADL of above 180 gsm is less soft and e.g. not comfortable for the wearer of the article. An ADL below 70 gsm does not ensure the good performance of the fluid-absorption articles especially in respect to fluid acquisition and dryness, e.g. as shown in higher rewet values.

The acquisition distribution layer (D), comprising at least 90% by weight of synthetic non-cellulose based fibers, preferable at least 95%, more preferred 98% most preferred 100% by weight of synthetic non-cellulose based fibers. In case of cellulose based fibers which absorb the liquid, the ADL structure becomes wet and heavy. When it's wet the pores of ADL required for liquid transport through the ADL may collapse, blocking the quick liquid passage and distribution into the core beneath, resulting in long acquisition times facilitating diaper leakage.

The acquisition distribution layer (D) preferably comprises a high loft synthetic non-cellulose based fibers carded web, which may be bonded by air, heat, calendaring and/or modifications such as resin additives and/or chemical binders or combinations thereof. It is preferred that the acquisition-distribution layer (D) is air-through bonded.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious Layer (A)" above.

Multiple fiber types and/or blends thereof are suitable, for example polyester, co-polyester, poly-propylene, polyethylene, polylactic acid or polyamide. Bi- or multi-component fibres comprising differring thermal responses can be used. They may improve functionality of the ADL (D) and/or 'soft feel' for the user of the hygienic article.

In case of a web the fibers are preferably hydrophilic. It may be derived from natural fibers, synthetic fibers or a combination of both. Known examples of synthetic fibers are found in the Chapter "Liquid-pervious Layer (A)"Further hydrophilic synthetic fibers are preferred. Hydrophilic synthetic fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers.

Alternatively a bundle of synthetic fibers acting as acquisition-distribution layer loosely distributed on top of the fluid-absorbent core may be used. Suitable synthetic fibers are of copolyester, polyamide, copolyamide, polylactic acid, polypropylene or polyethylene, viscose or blends thereof. Further bicomponent fibers can be used. The synthetic fiber component may be composed of either a single fiber type with a circular cross-section or a blend of two fibre types with different cross-sectional shapes. Synthetic fibers arranged in that way ensuring a very fast liquid transport and canalisation. Preferrably bundles of polyethylene fibers are used.

The synthetic non-cellulose based fibers suitable for use in acquisition distribution layer (D) have a strength suitable to be compressed e.g. in brick package, usually used for diapers, and able to return into the original conformation without fiber breakage or deformation caused by the pressure necessary for packaging.

An ADL useful in the inventive fluid-absorbent article is a multilayer nonwoven developed with airthrough bonded technology, skin-side having a voluminous structure, enhancing the fluid acquisition and distribution backside, wherein the layer at the skin-side preferably form the topsheet. Comprising at least two separate layers joint without any glue as e.g. purchased by Texsus as "Multitex".

Another ADL useful in the inventive absorbent article include high loft nonwovens developed with airthrough bonded technology. The ADL comprises a multilayer structure comprising a wide range of fiber mixtures. Such a multilayer nonwoven may be developed with airthrough bonded technology, skin-side having a voluminous structure, enhancing the fluid acquisition and distribution backside as e.g. purchased by Texsus as "Multifunctional Aquitex".

A further ADL useful in the inventive absorbent article comprises an asymmetric multilayered structure, with varied density of the fibers along the z-direction, ensuring a different upper and bottom side of the ADL, in terms of density, permeability, and absorbency. The upper part ensures a fast intake of the liquid, while the intermediate and bottom parts assure a wide distribution and temporary reserve for the fluid. For example ADL purchased by Texsus as "Vortex".

Another ADL suitable in the inventive fluid-absorbent article is a nonwoven comprising two outer fiber layers and at least one inner fiber layer having a different composition from that of the outer layers. The nonwoven comprises structural fibers and binding fibers, said binding fibers at least partially consisting of a polymer with a lower melting point than the structural fibers. Said nonwoven is densified by needling on both sides to a given depth while leaving an undensified central region.

According to another embodiment of the invention it is preferred that on top of the acquisition-distribution layer (D) between the upper layer (A) and the acquisition-distribution layer (D) a layer of curly fibres is placed. Curly fibres (cross-linked cellulose) is well known and disclosed as such in EP427316, U.S. Pat. No. 5,549,791, WO98/27262, U.S. Pat. No. 6,184,271, EP429112, and EP 427317. Due to the curly fibres the acquirement of discharged body fluids and the transfer and distribution of the fluid are improved. The curly fibres are hydrophilic. They bind discharged body fluids reversible. The discharged fluids are hold and distributed within the layer and not directly transferred to the acquisition-distribution layer and the absorbent core.

This lead to a very efficient fluid distribution in the absorbent article which results in very efficient utilization of the absorbent core in total.

In contrast a standard ATB (air-through bonded) ADL, used in absorbent articles consist of no layers and is constructed as one piece of non-woven web comprising a three dimensional network of fibers without a layered structure or structured pores distribution. The standard ADL has a homogeneous structure. As e.g. the pores of the standard ADL are not distributed with a special pattern or there are no layers or zones with different fiber density.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious Layer (A)" above.

Optional Tissue Layer (E)

An optional tissue layer is disposed immediately above and/or below (C).

The material of the tissue layer may comprise any known type of substrate, including webs, garments, textiles and films. The tissue layer may comprise natural fibers, such as cellulose, cotton, flax, linen, hemp, wool, silk, fur, hair and naturally occurring mineral fibers. The tissue layer may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the tissue layer comprises cellulose fibers.

Other Optional Components (F)

1. Leg Cuff

Typical leg cuffs comprising nonwoven materials which can be formed by direct extrusion processes during which the fibers and the nonwoven materials are formed at the same time, or by laying processes of preformed fibers which can be laid into nonwoven materials at a later point of time. Examples for direct extrusion processes include spunbonding, meltblowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-meltblown-spunbond (smms), spunbond-carded (sc), spunbond-airlaid (sa), meltblown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands. Preferred are leg cuffs from synthetic fibers showing the layer combinations sms, smms or smsms. Preferred are nonwovens with the density of 13 to 17 gsm. Preferably leg cuffs are provided with two elastic strands.

2. Elastics

The elastics are used for securely holding and flexibly closing the fluid-absorbent article around the wearers' body, e.g. the waist and the legs to improve containment and fit. Leg elastics are placed between the outer and inner layers or the fluid-absorbent article, or between the outer garment facing cover and the user facing bodyside liner. Suitable elastics comprising sheets, ribbons or strands of thermoplastic polyurethane, elastomeric materials, poly(ether-amide) block copolymers, thermoplastic rubbers, styrene-butadiene copolymers, silicon rubbers, natural rubbers, synthetic rubbers, styrene isoprene copolymers, styrene ethylene butylene copolymers, nylon copolymers, spandex fibers comprising segmented polyurethane and/or ethylene-vinyl acetate copolymer. The elastics may be secured to a substrate after being stretched, or secured to a stretched substrate. Otherwise, the elastics may be secured to a substrate and then elastisized or shrunk, e.g. by the application of heat.

3. Closing System

The closing system can include tape tabs, landing zone, elastomerics, pull ups and the belt system or combinations thereof.

At least a part of the first waist region is attached to a part of the second waist region by the closing system to hold the fluid-absorbent article in place and to form leg openings and the waist of the fluid-absorbent article. Preferably the fluid-absorbent article is provided with a reclosable closing system.

The closing system is either re-sealable or permanent, including any material suitable for such a use, e.g. plastics, elastics, films, foams, nonwoven substrates, woven substrates, paper, tissue, laminates, fiber reinforced plastics and the like, or combinations therof. Preferably the closing system includes flexible materials and works smooth and softly without irritating the wearer's skin.

One part of the closing elements is an adhesive tape, or comprises a pair of laterally extending tabs disposed on the lateral edges of the first waist region. Tape tabs are typically attached to the front body panel and extend laterally from each corner of the first waistband. These tape tabs include an adhesive inwardly facing surface which is typically protected prior to use by a thin, removable cover sheet.

Suitable tape tabs may be formed of thermoplastic polymers such as polyethylene, polyurethane, polystyrene, polycarbonate, polyester, ethylene vinyl acetate, ethylene vinyl alcohol, ethylene vinyl acetate acrylate or ethylene acrylic acid copolymers.

Suitable closing systems comprise further a hook portion of a hook and loop fastener and the target devices comprise the loop portion of a hook and loop fastener.

Suitable mechanical closing systems including a landing zone. Mechanical closing systems may fasten directly into the outer cover. The landing zone may act as an area of the fluid-absorbent article into which it is desirable to engage the tape tabs. The landing zone may include a base material and a plurality of tape tabs. The tape tabs may be embedded in the base material of the landing zone. The base material may include a loop material. The loop material may include a backing material and a layer of a nonwoven spunbond web attached to the backing material.

Thus suitable landing zones can be made by spunbonding. Spunbonded nonwoven are made from melt-spun fibers formed by extruding molten thermoplastic material. Preferred is bi-oriented polypropylene (BOPP), or brushed/closed loop in the case of mechanical closing systems.

Further, suitable mechanical closing systems including elasticomeric units serving as a flexible abdominal and/or dorsal discrete waist band, flexible abdomen and/or dorsal zones located at distal edge for fluid-absorbents articles, such as pants or pull-ups. The elasticomeric units enable the fluid-absorbent article to be pulled down by the wearer as e.g. a training pant.

Suitable pants-shaped fluid-absorbent article has front abdominal section, rear dorsal section, crotch section, side sections for connecting the front and rear sections in lateral direction, hip section, elastic waist region and liquid-tight outer layer. The hip section is arranged around the waist of the user. The disposable pants-shaped fluid-absorbent article (pull-up) has favorable flexibility, stretchability, leak-proof property and fit property, hence imparts excellent comfort to the wearer and offers improved mobility and discretion.

Suitable pull-ups comprising thermoplastic films, sheets and laminates having a low modulus, good tear strength and high elastic recovery.

Suitable closing systems may further comprise elastomerics for the production of elastic areas within the fastening devices of the fluid-absorbent article. Elastomerics provide a conformable fit of the fluid-absorbent article to the wearer at the waist and leg openings, while maintaining adequate performance against leakage.

Suitable elastomerics are elastomeric polymers or elastic adhesive materials showing vapor permeability and liquid barrier properties. Preferred elastomerics are retractable after elongation to a length equivalent to its original length.

Suitable closing systems further comprise a belt system, comprising waist-belt and leg-belts for flexibly securing the fluid-absorbent article on the body of the wearer and to provide an improved fit on the wearer. Suitable waist-belts comprising two elastic belts, a left elastic belt, and a right elastic belt. The left elastic belt is associated with each of the left angular edges. The right elastic belt associated with each of the right angular edges. The left and right side belts are elastically extended when the absorbent garment is laid flat.

Each belt is connected to and extends between the front and rear of the fluid-absorbent article to form a waist hole and leg holes.

Preferably the belt system is made of elastomerics, thus providing a conformable fit of the fluid-absorbent article and maintaining adequate performance against leakage.

Preferred closing systems are so-called "elastic ears" attached with one side of the ear to the longitudinal side edges located at the rear dorsal longitudinal edge of the chassis of the fluid-absorbent article. Commercially available fluid-absorbent articles include stretchable ears or side panels which are made from a stretchable laminate e.g. nonwoven webs made of mono- or bi-component fibers. Especially preferred closing systems are stretchable laminates comprising a core of several layers each of different fibrous materials, e.g. meltblown fibers, spunbond fibers, containing multicomponent fibers having a core comprising a first polymer having a first melt temperature and a sheath comprising a second polymer having a second melt temperature; and a web of an elastomeric material as top and bottom surfaces to form said laminate.

D. Fluid-Absorbent Article Construction

The present invention further relates to the joining of the components and layers, films, sheets, tissues or substrates mentioned above to provide the fluid-absorbent article. At least two, preferably all layers, films, sheets, tissues or substrates are joined.

Suitable fluid-absorbent articles include a single- or multiple fluid-absorbent core-system. Preferably fluid-absorbent articles include a single- or double fluid-absorbent core-system.

Suitable fluid-storage layers of the fluid-absorbent core comprising homogenous or in-homogenous mixtures of fibrous materials comprising water-absorbent polymer particles homogenously or in-homogenously dispersed in it or layers comprising only water-absorbent polymer particles without any fibrous materials. Suitable fluid-storage layers of the fluid-absorbent core also including a layered fluid-absorbent core-system comprising homogenous mixtures of fibrous materials and water-absorbent polymer particles or layers comprising only water-absorbent polymer particles without any fibrous materials.

In order to immobilize the water-absorbent polymer particles, the adjacent layers are fixed by the means of thermoplastic materials, thereby building connections throughout the whole surface or alternatively in discrete areas of junction. For the latter case, cavities or pockets are built carrying the water-absorbent particles. The areas of junction may have a regular or irregular pattern, e.g. aligned with the longitudinal axis of the fluid-absorbent core or in a pattern of polygons, e.g. pentagons or hexagons. The areas of junction itself may be of rectangular, circular or squared shape with diameters between about 0.5 mm and 2 mm. Fluid-absorbent articles comprising areas of junction show a better wet strength.

Suitable fluid-absorbent articles are including single or multi-core systems in any combination with other layers which are typically found in fluid-absorbent articles. Preferred fluid-absorbent articles include single- or double-core systems; most preferably fluid-absorbent articles include a single fluid-absorbent core.

The fluid-absorbent core typically has a uniform size or profile. Suitable fluid-absorbent cores can also have profiled structures, concerning the shape of the core and/or the content of water-absorbent polymer particles and/or the distribution of the water-absorbent polymer particles and/or the dimensions of the different layers if a layered fluid-absorbent core is present.

It is known that absorbent cores providing a good wet immobilization by combining several layers, e.g. a substrate layer, layers of water-absorbent polymer and layers of thermoplastic material. Suitable absorbent cores may also comprise tissue or tissue laminates. Known in the art are single or double layer tissue laminates formed by folding the tissue or the tissue laminate onto itself.

These layers or foldings are preferably joined to each e.g. by addition of adhesives or by mechanical, thermal or ultrasonic bonding or combinations thereof.

Thus, according to the number of layers or the height of a voluminous core, the resulting thickness of the fluid-absorbent core will be determined. Thus, fluid-absorbent cores may be flat as one layer (plateau) or have three-dimensional profile.

Generally the upper liquid-pervious layer (A) and the lower liquid-impervious layer (B) may be shaped and sized according to the requirements of the various types of fluid-absorbent articles and to accommodate various wearer's sizes. Thus, the combination of the upper liquid-pervious layer and the lower liquid-impervious layer may have all dimensions or shapes known in the art. Suitable combinations have an hourglass shape, rectangular shape, trapezoidal shape, t- or double t-shape or showing anatomical dimensions.

The construction of the products chassis and the components contained therein is made and controlled by the discrete application of hotmelt adhesives as known to people skilled in the art.

Examples would be e.g. Dispomelt 505B, Dispomelt Cool 1101, as well as other specific function adhesives manufactured by National Starch, Henkel or Fuller.

In order to ensure wicking of applied body fluids, preferred fluid-absorbent article show channels for better transport. Channels are formed by compressional forces of e.g. the top sheet against the fluid-absorbent core. Compressive forces may be applied e.g. by heat-treatment between two heated calendar rollers. As an effect of compression both on top sheet and fluid-absorbent core deform such that a channel is created. Body fluids are flowing along this channel to places where they are absorbed and leakage is prevented. Otherwise, compression leads to higher density; this is the second effect of the channel to canalize insulted fluids. Additionally, compressive forces on diaper construction improve the structural integrity of the fluid-absorbent article.

A possible embodiment of the present invention is shown in FIG. 7.

Thus according to one embodiment, a fluid-absorbent article according to the invention comprising
- (A) an upper liquid-pervious layer comprising a spunbond layer (coverstock)
- (B) a lower liquid-impervious layer comprising a composite of a breathable polyethylene film
- (C) a single fluid-absorbent core (C) between (A) and (B) comprising a homogeneous mixture of water-absorbent polymer particles and cellulose fibres
- (D) an acquisition-distribution layer (D) between (A) and (C) having a size smaller than the fluid absorbent core (C).

According to the invention it is preferred that the fluid-absorbent article comprising
- (A) an upper liquid-pervious layer,
- (B) a lower liquid-impervious layer, (C) a fluid-absorbent core between (A) and (B) comprising at least 60% by weight of fluid-absorbent polymer particles and not more than 40% by weight of fibrous material, based on the sum of fluid-absorbent polymer particles and fibrous material;

(D) an acquisition-distribution layer between (A) and (C) comprising at least 90% by weight of synthetic fibers and not more than 10% by weight of cellulose based fibers, based on the sum of synthetic fibers and cellulose based fibers, (E) an optional tissue layer disposed immediately above and/or below (C); and (F) other optional components, wherein the basis weight of the acquisition-distribution layer (D) is at least 70 gsm and the fluid-absorbent polymer particles have a saline flow conductivity (SFC) of less than $5 \times 10^{-7}$ cm$^3$s/g and an AUHL of less than 15 g/g.

Preferably the acquisition-distribution layer (D) is a nonwoven web comprising a three dimensional network of fibers.

The inventive fluid-absorbent article with a fluid-absorbent core comprising non-permeable non-surface postcrosslinked fluid-absorbent particles (the fluid-absorbent particles preferably have a SFC of less than $5 \times 10^{-7}$ cm$^3$s/g, a CRC of at least 35 g/g, preferably 40 g/g and an AUHL of less than 15 g/g) in combination with ADLs having a basis weight of at least 70 gsm, preferably at least 80 gsm showing similar or even better rewet and liquid acquisition time than fluid-absorbent articles with cores containing permeable surface-postcrosslinked fluid-absorbent particles having an SFC of at least $20 \times 10^{-7}$ cm$^3$s/g, in combination with a standard ADL of a basis weight of less than 70 gsm. Usually in fluid-absorbent articles ADLs of a basis weight of 60 to 40 gsm are used.

The fluid-absorbent article according to the invention despite the fact, that preferred embodiments contain non-surface-post-crosslinked water-absorbent polymer particles show no increased gel-blocking compared to fluid-absorbent articles containing more permeable water-absorbent polymer particles.

Surprisingly the use of ADLs with a basis weight of at least 70 gsm, preferably at least 80 gsm, more preferably at least 90 gsm, most preferably at least 100 gsm, even more preferably at least 120 gsm usually not above 180 g/m$^2$ in fluid-absorbent articles seems to take over the permeability-function of the fluid-absorbent particles.

Surprisingly the advantage of the permeability of the surface-postcrosslinked fluid-absorbent particles itself in respect to the performance of the fluid-absorbent articles, especially in respect to at least one of the features such as e.g. rewet under load and liquid acquisition time, is even lost or rather turned to a negative effect as the non-surface-post-crosslinked water-absorbent polymer particles usually provide a much higher capacity in absorbent articles.

According to the invention it is therefore also possible to provide fluid-absorbent articles with reduced amounts of fluid-absorbent particles.

At least a similar performance of the fluid-absorbent article is achieved with less superabsorbent in terms of liquid acquisition time and/or rewet under load. A reduction of at least 5%, preferably at least 10%, more preferably at least 15%, most preferably of at least 20% up to a maximum of 30% of the amount of the non-surface postcrosslinked water-absorbent polymer particles present in the inventive fluid absorbent article with an ADL with a basis weight of at least 70 gsm, preferably at least 80 gsm, compared to fluid-absorbent articles comprising standard ADL with a basis weight of less than 70 gsm are achieved.

Preferably for the inventive fluid-absorbent article the liquid acquisition time of the 1$^{st}$ insult is below 60 sec, preferably below 55 sec.

The inventive absorbent article does not only allow the reduction of the amount of water-absorbent polymer particles used but also requires the use of non-surface crosslinked water-absorbent polymer particles. This means less steps in the production process of the particles and overall less consumption of energy and resources and a more sustainable absorbent article.

Methods

The measurements should, unless stated otherwise, be carried out at an ambient temperature of 23±2° C. and a relative atmospheric humidity of 50±10%. The water-absorbent polymers are mixed thoroughly before the measurement.

The "WSP" standard test methods are described in: "Standard Test Methods for the Nonwovens Industry", jointly issued by the "Worldwide Strategic Partners" EDANA (European Disposables and Nonwovens Association, Avenue Eugene Plasky, 157, 1030 Brussels, Belgium, www.edana.org) and INDA (Association of the Nonwoven Fabrics Industry, 1100 Crescent Green, Suite 115, Cary, N.C. 27518, U.S.A., www.inda.org). This publication is available both from EDANA and INDA.

Residual Monomers

The level of residual monomers in the water-absorbent polymer particles is determined by the EDANA recommended test method No. WSP 210.3 (11) "Residual Monomers".

Particle Size Distribution

The particle size distribution of the water-absorbent polymer particles is determined by the EDANA recommended test method No. WSP 220.3 (11) "Particle Size Distribution".

The average particle diameter ($d_{50}$) here is the value of the mesh size which gives rise to a cumulative 50% by weight.

The degree of polydispersity α of the particle size particle is calculated by $\alpha = (d_{84.13} - d_{15.87})/(2 \times d_{50})$ wherein $d_{15.87}$ and $d_{84.13}$ is the value of the mesh size which gives rise to a cumulative 15.87% respective 84.13% by weight.

Moisture Content

The moisture content of the water-absorbent polymer particles is determined by the EDANA recommended test method No. WSP 230.3 (11) "Mass Loss Upon Heating".

Free Swell Capacity (FSC)

The free swell capacity of the water-absorbent polymer particles is determined by the EDANA recommended test method No. WSP 240.3 (11) "Free Swell Capacity in Saline, Gravimetric Determination", wherein for higher values of the free swell capacity larger tea bags have to be used.

Centrifuge Retention Capacity (CRC)

The centrifuge retention capacity of the water-absorbent polymer particles is determined by the EDANA recommended test method No. WSP 241.3 (11) "Fluid Retention Capacity in Saline, After Centrifugation", wherein for higher values of the centrifuge retention capacity larger tea bags have to be used.

Absorption Under Load (AUL)

The absorption under load of the water-absorbent polymer particles is determined by the EDANA recommended test method No. WSP 242.3 (11) "Gravimetric Determination of Absorption Under Pressure".

Absorption Under High Load (AUHL)

The absortion under high load of the water-absorbent polymer particles is determined analogously to the EDANA recommended test method No. WSP 242.3 (11) "Gravimetric Determination of Absorption Under Pressure", except using a weight of 49.2 g/cm$^2$ instead of a weight of 21.0 g/cm$^2$.

Bulk Density

The bulk density of the water-absorbent polymer particles is determined by the EDANA recommended test method No. WSP 250.3 (11) "Gravimetric Determination of Density".

Extractables

The level of extractable constituents in the water-absorbent polymer particles is determined by the EDANA recommended test method No. WSP 270.3 (11) "Extractables".

Roundness or Sphericity

The roundness (or sphericity (SPHT)) is determined with the PartAn® 3001 L Particle Analysator (Microtrac Europe GmbH; Meerbusch; Germany). The roundness is defined as $$\text{Roundness} = \frac{4\pi A}{U^2}$$

where A is the cross-sectional area and U is the cross-sectional circumference of the polymer particles. The roundness is the volume-average roundness.

For the measurement, the product is introduced through a funnel and conveyed to the falling shaft with a metering channel. While the particles fall past a light wall, they are recorded selectively by a camera. The images recorded are evaluated by the software in accordance with the parameters selected.

Saline Flow Conductivity (SFC)

The saline flow conductivity of a swollen gel layer under a pressure of 0.3 psi (2070 Pa) is determined, as described in EP 2 535 698 A1, with a weight of 1.5 g of water-absorbing polymer particles as a urine permeability measurement (UPM) of a swollen gel layer. The flow is detected automatically.

The saline flow conductivity (SFC) is calculated as follows:

$$SFC\ [cm^3 s/g] = (Fg(t=0) \times L_0)/(d \times A \times WP)$$

where $Fg(t=0)$ is the flow of NaCl solution in g/s, which is obtained using linear regression analysis of the Fg(t) data of the flow determinations by extrapolation to t=0, $L_0$ is the thickness of the gel layer in cm, d is the density of the NaCl solution in g/cm$^3$, A is the area of the gel layer in cm$^2$, and WP is the hydrostatic pressure over the gel layer in dynes/cm$^2$.

Vortex 50.0±1.0 ml of 0.9% NaCl solution are added into a 100 ml beaker. A cylindrical stirrer bar (30×6 mm) is added and the saline solution is stirred on a stir plate at 60 rpm. 2.000±0.010 g of water-absorbent polymer particles are added to the beaker as quickly as possible, starting a stop watch as addition begins. The stopwatch is stopped when the surface of the mixture becomes "still" that means the surface has no turbulence, and while the mixture may still turn, the entire surface of particles turns as a unit. The displayed time of the stopwatch is recorded as Vortex time

Color Value (CIE Color Numbers [L, a, b])

Measurement of the color value is done by means of a colorimeter model "LabScan XE S/N LX17309" (Hunter-Lab; Reston; U.S.A.) according to the CIELAB procedure (Hunterlab, Volume 8, 1996, Issue 7, pages 1 to 4). Colors are described by the coordinates L, a, and b of a three-dimensional system. L characterizes the brightness, whereby L=0 is black and L=100 is white. The values for a and b describe the position of the color on the color axis red/green resp. yellow/blue, whereby positive a values stand for red colors, negative a values for green colors, positive b values for yellow colors, and negative b values for blue colors.

The measurement of the color value is in agreement with the tristimulus method according to DIN 5033-6.

Accelerated Aging Test

Measurement 1 (Initial color): A plastic dish with an inner diameter of 9 cm is overfilled with superabsorbent polymer particles. The surface is flattened at the height of the petri dish lip by means of a knife and the CIE color values and the HC 60 value are determined.

Measurement 2 (after aging): A plastic dish with an inner diameter of 9 cm is overfilled with superabsorbent polymer particles. The surface is flattened at the height of the petri dish lip by means of a knife. The plastic dish (without a cover) is then placed in a humidity chamber at 60° C. and a relative humidity of 86%. The plastic dish is removed from the humidity chamber after 7, 14, and 21 days, cooled down to room temperature and the CIE color values are determined.

The EDANA test methods are obtainable, for example, from the EDANA, Avenue Eugene Plasky 157, B-1030 Brussels, Belgium.

Rewet Under Load (RUL) and Acquisition Time

The test determines the amount of fluid a fluid-absorbent article will release after being maintained at a pressure of 0.7 psi (49.2 g/cm$^2$) for 5 min following multiple separate insults. The rewet under load is measured by the amount of fluid the fluid-absorbent article releases under pressure. The rewet under load is measured after each insult.

The fluid-absorbent article is clamped nonwoven side upward onto the inspection table. The insult point (pee point) is marked accordingly with regard to the type and gender of the diaper to be tested (i.e. in the centre of the core for girl, 2.5 cm towards the front for unisex and 5 cm towards the front for boy). A 3.64 kg circular weight (10 cm diameter) having a central opening (2.3 cm diameter) with perspex tube is placed with on the previously marked insult point.

For the primary insult 75 g of aqueous saline solution (0.9% by weight) is poured into the perspex tube in one shot. Amount of time needed for the fluid to be fully absorbed into the fluid-absorbent article is recorded—it is an acquisition time, reported in seconds. After 5 minutes have elapsed, the load is removed and the stack of 10 filter papers (Whatman®) having 9 cm diameter and known dry weight (W1) is placed over the insult point on the fluid-absorbent article. On top of the filter paper, the 2.5 kg weight with 8 cm diameter is added. After 2 minutes have elapsed the weight is removed and filter paper reweighed giving the wet weight value (W2).

The rewet under load is calculated as follows:

$RUL\ [g]=W2-W1$

For the rewet under load of the secondary and following insults the procedure for the primary insult is repeated. For each following insults 2", 3" and 4" 75 g of aqueous saline solution (0.9% by weight) and 20, 30, 40 filter papers respectively are used.

EXAMPLES

Preparation of the Fluid-Absorbent Polymer Particles

The following polymer particles were used:
HySorb® B7085 or available from BASF Antwerpen N.V., Belgium
HySorb® T9700 available from BASF Corporation, Freeport, USA
Surface-crosslinked water-absorbent polymers produced by droplet polymerization as described in Example 2
Water-absorbent polymers without surface crosslinking produced by kneader polymerization as described in Example 3
Surface crosslinked water-absorbent polymers produced by kneader polymerization as described in Example 4
Features and absorption profiles of all polymer particles are summarized in Table 9.

Example 1—Droplet Polymerization Basepolymer

The production of the water-absorbing polymer particles by droplet polymerization is described in detail in WO 2016/134905.

The process was performed analogously according to Example 1 of WO 2016/134905: The process was performed in a concurrent spray drying plant with an integrated fluidized bed (27) as shown in FIG. 1 (FIG. 1 of WO 2016/134905). The reaction zone (5) had a height of 22 m and a diameter of 3.4 m. The internal fluidized bed (IFB) had a diameter of 3 m and a weir height of 0.25 m.

The drying gas was fed via a gas distributor (3) at the top of the spray dryer. The drying gas was partly recycled (drying gas loop) via a cyclone as dust separation unit (9) and a condenser column (12). The drying gas was nitrogen that comprises from 1% to 4% by volume of residual oxygen. Prior to the start of polymerization the drying gas loop was filled with nitrogen until the residual oxygen was below 4% by volume. The gas velocity of the drying gas in the reaction zone (5) was 0.79 m/s. The pressure inside the spray dryer was 4 mbar below ambient pressure.

Figure 2:
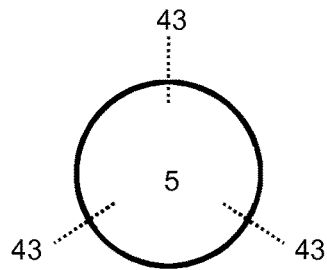
Figure 3:
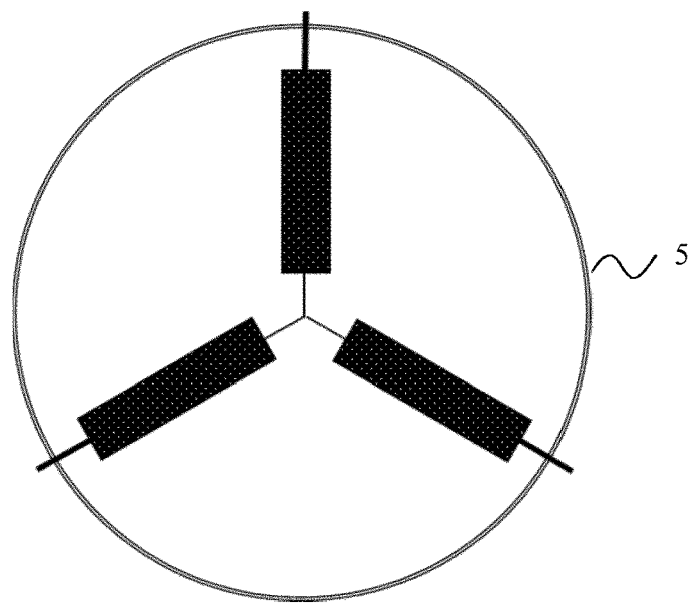

The temperature of the gas leaving the reaction zone (5) was measured at three points around the circumference at the end of the cylindrical part of the spray dryer as shown in FIG. 2 (FIG. 3 of WO 2016/134905). Three single measurements (43) were used to calculate the average temperature (spray dryer outlet temperature). The drying gas loop was heated up and the dosage of monomer solution is started up. From this time the spray dryer outlet temperature was controlled to 122° C. by adjusting the gas inlet temperature via the heat exchanger (20). The gas inlet temperature was 167° C. and the steam content of the drying gas is shown in Tab. 1.

The product accumulated in the internal fluidized bed (27) until the weir height was reached. Conditioned internal fluidized bed gas having a temperature of 112° was fed to the internal fluidized bed (27) via line (25). The gas velocity of the internal fluidized bed gas in the internal fluidized bed (27) was 0.65 m/s. The residence time of the product was 150 min. The temperature of the water-absorbent polymer particles in the internal fluidized bed (27) was 80° C.

The spray dryer offgas was filtered in cyclone as dust separation unit (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas. The temperature and the steam content of the gas leaving the condenser column (12) are shown in Tab. 1. The water inside the condenser column (12) was set to an alkaline pH by dosing sodium hydroxide solution to wash out acrylic acid vapors.

The gas leaving the condenser column (12) was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm. The weight amounts of overs/lumps are summarized in Tab. 3.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (31) and (32) via lines (33) and (34) as shown in FIG. 1 (FIG. 1 of WO 2016/134905. Sodium peroxodisulfate solution having a temperature of 20° C. was added via line (33) and [2,2'- azobis[2-(2-imidazolin-2-yl)propane]dihydrochloride solution together with Brüggolite® FF7 and Blancolen® HP having a temperature of 10° C. was added via line (34). Each initiator was pumped in a loop and dosed via control valves to each dropletizer unit. A second filter unit having a mesh size of 140 µm was used after the static mixer (32). For dosing the monomer solution into the top of the spray dryer three dropletizer units were used as shown in FIG. 3 (FIG. 4 of WO 2016/134905).

Figure 4:
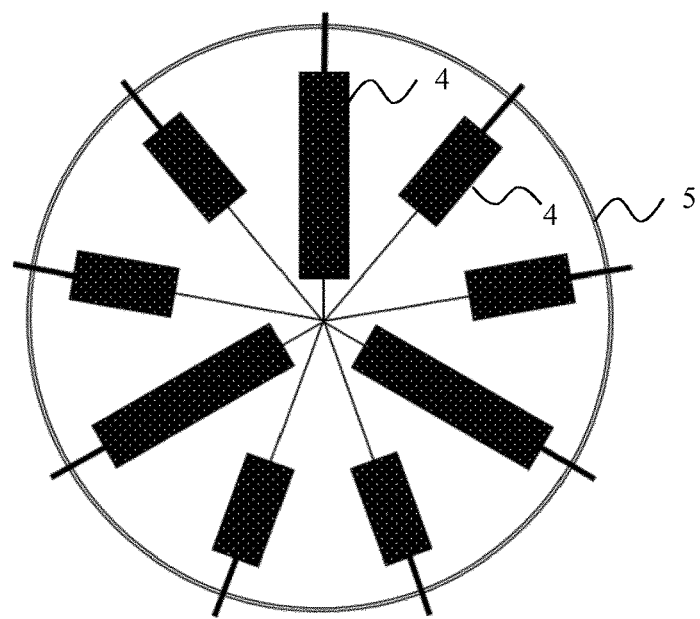
Figure 5:
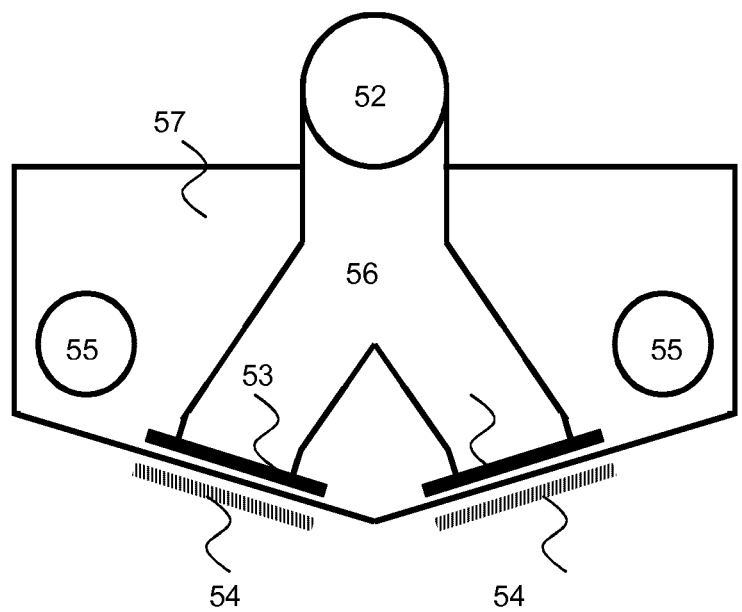

A dropletizer unit consisted of an outer pipe (47) having an opening for the dropletizer cassette (49) as shown in FIG. 4 (FIG. 5 of WO 2016/134905). The dropletizer cassette (49) was connected with an inner pipe (48). The inner pipe (48) having a PTFE block (50) at the end as sealing can be pushed in and out of the outer pipe (47) during operation of the process for maintenance purposes.

The temperature of the dropletizer cassette (49) was controlled to 8° C. by water in flow channels (55) as shown in FIG. 5 (FIG. 8 of WO 2016/134905). The dropletizer cassette (49) had 256 bores having a diameter of 170 µm and a bore spacing of 15 mm. The dropletizer cassette (49) consisted of a flow channel (56) having essential no stagnant volume for homogeneous distribution of the premixed monomer and initiator solutions and one droplet plate (53). The droplet plate (53) had an angled configuration with an angle of 3°. The droplet plate (53) was made of stainless steel and had a length of 630 mm, a width of 128 mm and a thickness of 1 mm.

The feed to the spray dryer consisted of 9.56% by weight of acrylic acid, 33.73% by weight of sodium acrylate, 0.011% by weight of 3-tuply ethoxylated glycerol Triacrylate (purity approx. 85% by weight), 0.071% by weight of [2,2'-azobis[2-(2-imidazolin-2-yl)propane]dihydrochloride, 0.0028% by weight of Brüggolite® FF7 (Bruggemann Chemicals; Heilbronn; Germany), 0.071% by weight of Blancolene® HP (Brüggemann Chemicals; Heilbronn; Germany) 0.054% by weight of sodiumperoxodisulfate and water. The degree of neutralization was 73%. The feed per bore was 1.4 kg/h.

The resulting water-absorbent polymer particles were analyzed. The conditions and results are summarized in Tab. 1 to 3.

TABLE 1

Process conditions of the polymerization for examples 1 to 7

| Example | Steam Content CC kg/kg | Steam Content GD kg/kg | T gas inlet °C. | T gas outlet °C. | T gas IFB °C. | T IFB °C. | T CC °C. | T GDU °C. |
|---|---|---|---|---|---|---|---|---|
| 1 | 0.1100 | 0.0651 | 167 | 122 | 112 | 80 | 54 | 45 |

Steam Content CC: steam content of the gas leaving the condenser column (12)
Steam Content GD: steam content of the gas prior to the gas distributor (3)
T gas inlet: temperature of the gas prior to the gas distributor (3)
T gas outlet: temperature of the gas leaving the reaction zone (5)
T gas IFB temperature of the gas entering the internal fluidized bed (27) via line (25)
T IFB: temperature of the water-absorbent polymer particles in the fluidized bed (27)
T CC: temperature of the gas leaving the condenser column (12)
T GDU: temperature of the gas leaving the gas drying unit (37)

TABLE 2

Properties of the water-absorbent polymer particles (base polymer)

| Example | Bulk Density g/cm³ | CRC g/g | AUL g/g | Residual Monomers Ppm | Extractables wt. % | Moisture wt. % | L | a | b |
|---|---|---|---|---|---|---|---|---|---|
| 1 | 62.5 | 69.8 | 7.5 | 6300 | 11.8 | 8.2 | 94.1 | 1.5 | 2.0 |

TABLE 3

Particles Size Distribution (PSD) of the water-absorbent polymer particles (base polymer), measured by sieve fraction analysis

| Example | 0-100 µm wt % | 100-200 µm wt % | 200-250 µm wt % | 250-300 µm wt % | 300-400 µm wt % | 400-500 µm wt % | 500-600 µm wt % | 600-850 µm wt % | 850-1000 µm wt % | >1000 µm wt % |
|---|---|---|---|---|---|---|---|---|---|---|
| 1 | 0.0 | 0.5 | 3.3 | 6.7 | 26.3 | 31.9 | 17.1 | 13.3 | 0.8 | 0.1 |

General Description of Surface Crosslinking

Figure 6:
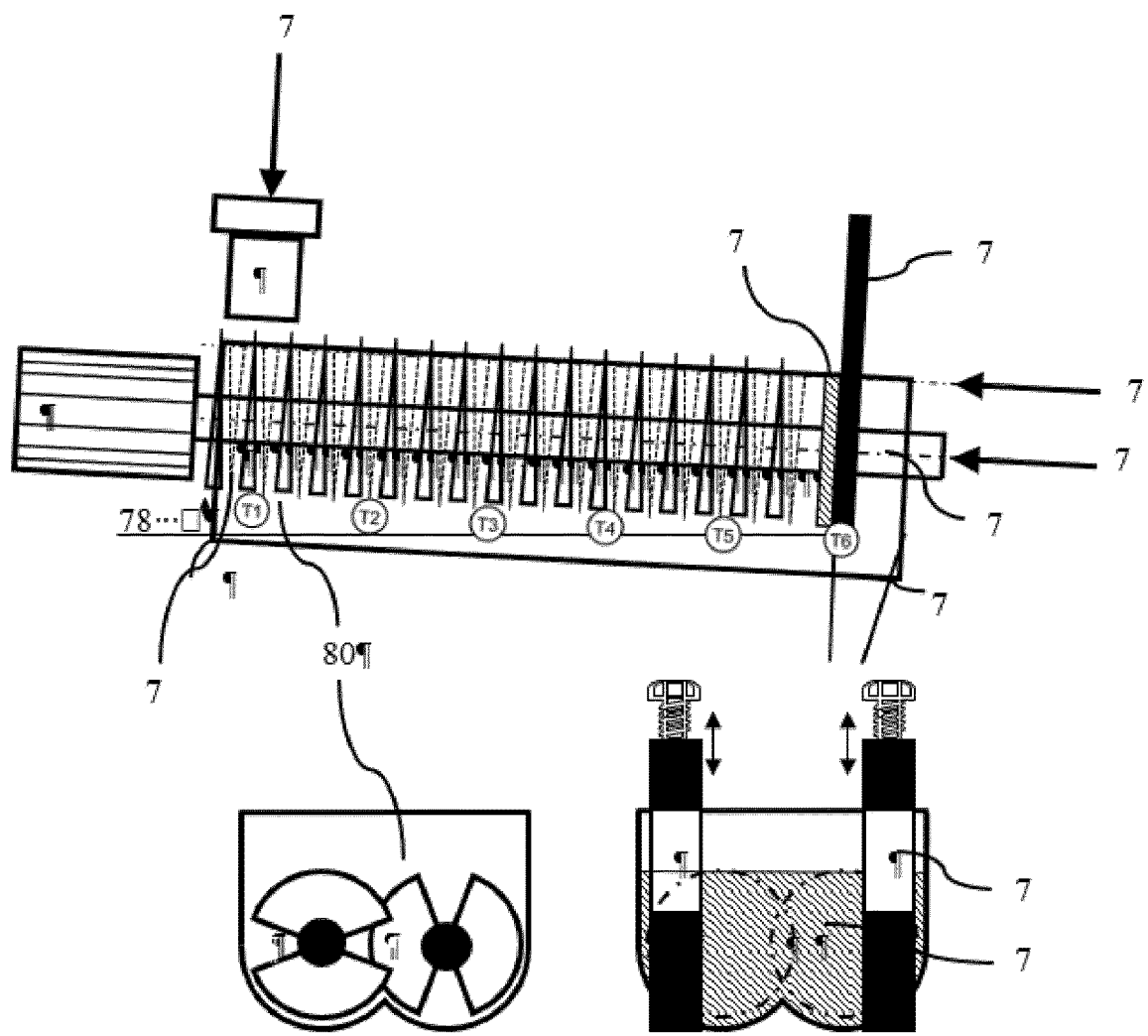

In a Schugi Flexomix® (model Flexomix 160, manufactured by Hosokawa Micron B.V., Doetinchem, the Netherlands) with a speed of 2000 rpm, the water absorbent base polymer was coated with a surface-postcrosslinker solution by using 3 round spray nozzle systems (model Gravity-Fed Spray Set-ups, External Mix Typ SU4, Fluid Cap 60100 and Air Cap SS-120, manufactured by Spraying Systems Co, Wheaton, Illinois, USA) and then filled via base polymer feed (70) and dried in a thermal dryer (65) (model NPD 5W-18, manufactured by GMF Gouda, Waddinxveen, the Netherlands) with a speed of the shaft (76) of 6 rpm. The thermal dryer (65) has two paddles with a shaft offset of 90° (80) and a fixed discharge zone (71) with two flexible weir plates (73). Each weir has a weir opening with a minimal weir height at 50% (75) and a maximal weir opening at 100% (74) as shown in FIG. 6 (FIG. 15 of WO 2016/134905).

The inclination angle α (78) between the floor plate and the thermal dryer was approx. 3°. The weir height of the thermal dryer was between 50 to 100%, corresponding to a residence time of approx. 40 to 150 min, by a product density of approx. 700 to 750 kg/m³. The product temperature in the thermal dryer was in a range of 120 to 165° C. After drying, the surface-postcross-linked polymer was transported over discharge cone (77) in a cooler (model NPD 5W-18, manufactured by GMF Gouda, Waddinxveen, the Netherlands), to cool down the surface postcross-linked polymer to approx. 60° C. with a speed of 11 rpm and a weir height of 145 mm. After cooling, the material was sieved with a minimum cut size of 150 μm and a maximum cut size of 850 μm.

Example 2

Surface crosslinking of base polymer prepared in example 1.

Ethylene carbonate, water, Span® 20 (Croda, Nettetal, Germany)), aqueous aluminum lactate (22% by weight) were premixed and used as surface-postcrosslinker solution as summarized in Tab. 5. As aluminum lactate, Lothragon® Al 220 (manufactured by Dr. Paul Lohmann GmbH, Emmerthal, Germany) was used.

4.3 wt % of a 0.05% aqueous solution of Plantacare® 818 UP solution (dry, manufactured by BASF SE) and 4.3 wt % of a 0.025% aqueous solution of Plantacare® 818 UP were additionally added into the cooler using two nozzles in the first third of the cooler. Both solution having a temperature of approx. 25° C. The nozzles were placed below the product bed.

The resulting water-absorbent polymer particles were analyzed. The trial conditions and results are summarized in Tab. 4 to 8.

TABLE 4

Process conditions of the thermal dryer for the surface postcrosslinking (SXL)

| Example | Product Temp. Set Value | Steam Pressure Wave | Steam Pressure Jacket | Heater T1 | Heater T2 | Heater T3 | Heater T4 | Heater T5 | Heater T6 | Through-put | Heater Weir | No. of Nozzles | Pos. of Nozzles |
|---|---|---|---|---|---|---|---|---|---|---|---|---|---|
| Unit | ° C. | bar | Bar | ° C. | ° C. | ° C. | ° C. | ° C. | ° C. | kg/h | % | | |
| 2 | 140 | 3.7 | 3.6 | 76 | 104 | 119 | 129 | 130 | 140 | 470 | 80 | 3 | 90/180/270° |

TABLE 5

Surface-postcrosslinker formulation of the thermal treatment in the heater and remoistening in the cooler

| | | | | | | Cooler | |
|---|---|---|---|---|---|---|---|
| | | | SXL | | | 0.05 wt % | 0.025 wt % |
| Example | Base polymer | EC bop % | Water bop % | Al-lactate (dry) bop % | Plantacare ® UP 818 (dry) bop ppm | aq. solution of Plantacare ® UP 818 (dry) bop % | aq. solution of Plantacare ® UP 818 (dry) bop % |
| 2 | Example 1 | 2.0 | 5.0 | 0.2 | 25 | 4.3 | 4.3 |

EC: Ethylene carbonate;
bop: based on polymer

TABLE 6

Physical properties of the polymer particles after surface-postcrosslinking

| Example | CRC g/g | AUL g/g | AUHL g/g | Moisture % | Residual Monomers Ppm | Extractables % | Bulk Density g/100 ml |
|---|---|---|---|---|---|---|---|
| 2 | 45.4 | 30.8 | 15.8 | 1.2 | 739 | 6.5 | 76 |

TABLE 7

Particle size distribution of the polymer particles after surface-postcrosslinking - Sieve fractions

| Example | <150 μm % | >150 μm % | >200 μm % | >250 μm % | >300 μm % | >400 μm % | >500 μm % | >600 μm % | >710 μm % |
|---|---|---|---|---|---|---|---|---|---|
| 2 | 0.1 | 0.4 | 2.3 | 5.9 | 32.5 | 35.3 | 16.9 | 5.7 | 0.9 |

TABLE 8

Color stability of the polymer particles after surface-postcrosslinking (Accelerated Aging Test)

| | 0 d | | | 7 d | | | 14 d | | | 21 d | | |
|---|---|---|---|---|---|---|---|---|---|---|---|---|
| Example | L | A | B | L | A | B | L | a | b | L | A | b |
| 2 | 94.1 | −1.7 | 7.8 | 86.7 | −1.3 | 7.7 | 85.2 | −1.3 | 8.5 | 83.0 | −1.2 | 9.0 |

Example 3 Production of Water-Absorbing Polymer-Base Polymer

The production of the water-absorbing polymer particles is described in detail in WO14/005860. A base polymer was prepared analogously to the continuous kneader process described in WO 01/38402 A1, in a List Contikneter reactor having a capacity of 6.3 m³ (LIST AG, Arisdorf, Switzerland). For this purpose, acrylic acid was neutralized continuously with sodium hydroxide solution and diluted with water, such that the degree of neutralization of the acrylic acid was 72 mol % and the solids content (=sodium acrylate and acrylic acid) of this solution was approx. 42.6% by weight. The polyethylene glycol 4000 (Pluriol E4000, BASF SE) in amount of 0.75% by weight based on acrylic acid was mixed with aqueous monomer solution. The crosslinker used was acrylated glyceryl triacrylate with triple ethoxylation overall (Gly-3 EO-TA), which had been prepared according to US 2005/0176910, in an amount of 0.186% by weight based on acrylic acid monomer. The crosslinker was added continuously to the monomer stream. For the calculation of the acrylic acid monomer content, the sodium acrylate present was considered theoretically as acrylic acid. The initiation was effected by likewise continuous addition of aqueous solutions of the initiators sodium persulfate (0.192% by weight based on acrylic acid monomer), hydrogen peroxide (0.0006% by weight based on acrylic acid monomer) and ascorbic acid (0.0025% by weight based on acrylic acid monomer).

The polymer gel obtained was dried on a belt drier, then the drier cake was crushed, ground by means of a roll mill and finally screened off to a particle size of 150 to 850 μm.

Example 4

Surface Crosslinking of Base Polymer Prepared in Example 3

The base polymer from example 3 was coated with a surface-crosslinking solution in a Schugi Flexomix® (model Flexomix 160, manufactured by Hosokawa Micron B.V., Doetinchem, the Netherlands) by using 3 round spray nozzle systems. As surface-postcrosslinker solution the mixture of 0.02 wt. % Denacol® EX-810 (ethylenglycoldiglycidylether), 3 wt. % water, 0.05 wt. % aluminiumsulfate and 2 wt. % isopropanol, was used. Amount of all compounds was calculated by weight based on base polymer. The sprayed polymer was directly dried in a thermal dryer (model NPD 5W-18, manufactured by GMF Gouda, Waddinxveen, the Netherlands). The throughput rate of the polymer in the dryer was 500 kg/h. The weir height of the thermal dryer was 75%, and the product temperature in the thermal dryer was in a range of 120 to 140° C. After drying, the surface-postcrosslinked polymer was transported to a NARA cooler (GMF Gouda, Waddinxveen, the Netherlands), to cool down the surface postcrosslinked polymer to approx. 60° C. with a speed of 11 rpm and a weir height of 145mm. After cooling, the material was sieved with a minimum cut size of 45 μm and a maximum cut size of 710 μm.

The properties of the water-absorbent polymers thus prepared are summarized in Table 9.

TABLE 9

Physical properties of the polymer particles used for absorbent core preparation.

| Product sample | FSC (g/g) | CRC (g/g) | AUNL 0.0 psi (g/g) | AUL 0.3 psi (g/g) | AUHL 0.7 psi (g/g) | SFC | Vortex (s) |
|---|---|---|---|---|---|---|---|
| HySorb ® B7085 | 46.3 | 29.0 | 42.2 | 28.9 | 22.5 | 26 | 68 |
| HySorb ® T9700 | 54.2 | 31.6 | 46.1 | 26.4 | 19.4 | 28 | 100 |
| Example 2 | 62.7 | 45.4 | 58.7 | 30.8 | 15.8 | 0 | 63 |
| Example 3 | 56.8 | 46.9 | 48.1 | 7.5 | 6.4 | 0 | 43 |
| Example 4 | 56.1 | 37.8 | 49.5 | 32.8 | 23.0 | 3 | 59 |

Preparation of the Fluid-Absorbent Pad

Example 5 Fluid-Absorbent Pad

The fluid-absorbent pad comprises single core system having a rectangular size of 41 cm×10 cm. The fluid-absorbent pad comprises a multi-layered system of spun-bond layer coverstock as top sheet (A), layered, high loft acquisition distribution layer (D) and fluid absorbent core (C) made of fluff/SAP mixtures.

The total weight of fluff pulp (cellulose fibers) is 7 g. The density of the fluid-absorbent core is in average 0.25-0.30 g/cm³. The basis weight of the core is 488 g/m². The fluid-absorbent core holds 65% by weight uniformly distributed fluid-absorbent polymer particles from Example 3;

the quantity of the fluid-absorbent polymer particles within the fluid-absorbent core is 13 g.

The acquisition-distribution layer (D) is rectangular shaped of a size of 16 cm×9 cm and placed on the absorbent core that way, that the middle point of the ADL covers the pee point. The pee point is marked 2.5 cm towards the front from the center of the absorbent core.

The following acquisition distribution layers were used:
The following acquisition distribution layers were used:
Example 5 a (comparative) air-through bonded Acquitex (Texsus, Italy) having basis weight of 50 g/m² was used.
Example 5 b—Multifunctional Acquitex (Texsus, Italy) having basis weight of 80 g/m²
Example 5 c—high loft Vortex (Texsus, Italy) having basis weight of 80 g/m²
Example 5 d—high loft Vortex (Texsus, Italy) having basis weight of 100 g/m²

Acquisition time under load and rewet value of the fluid absorbent pads are determined and results are summarized in Table 10.

Example 6—Comparative

A fluid-absorbent pad of Example 5 was repeated, except that a fluid absorbent polymer particles prepared in example 3 were replaced by the fluid absorbent polymer particles described in example 2.

The following acquisition distribution layers were used:
Example 6 c
air-through bonded Acquitex (Texsus, Italy) having basis weight of 50 g/m² was used.
Example 6 b—Multifunctional Acquitex (Texsus, Italy) having basis weight of 80 g/m²
Example 6 c—high loft Vortex (Texsus, Italy) having basis weight of 80 g/m²
Example 6 d—high loft Vortex (Texsus, Italy) having basis weight of 100 g/m²

Acquisition time under load and rewet value of the fluid absorbent pads are determined and results are summarized in Table 10.

Example 7—Comparative

A fluid-absorbent pad of Example 5 was repeated, except that a fluid absorbent polymer particles prepared in example 3 were replaced by the fluid absorbent polymer particles described in example 4.

The following acquisition distribution layers were used:
Example 7 a
pair-through bonded Acquitex (Texsus, Italy) having basis weight of 50 g/m² was used.
Example 7 b—Multifunctional Acquitex (Texsus, Italy) having basis weight of 80 g/m²
Example 7 fc—high loft Vortex (Texsus, Italy) having basis weight of 80 g/m²
Example 7 d—high loft Vortex (Texsus, Italy) having basis weight of 100 g/m²

Acquisition time under load and rewet value of the fluid absorbent pads are determined and results are summarized in Table 10.

Example 8—Comparative

A fluid-absorbent pad of Example 5 was repeated, except that fluid absorbent polymer particles prepared in example 3 were replaced by commercially available, highly permeable Hysorb® 9700.

Hysorb® 9700 consists of irregular shaped fluid-absorbent polymer particles produced by gel polymerization exhibiting the following features and absorption profile:
CRC of 31 g/g
SFC of 28 $10^{-7}$ cm³s/g
AUHL of 19 g/g
AUL of 26 g/g
FSC of 54 g/g
Vortex of 100 sec The following acquisition distribution layers were used:
Example 8 a
air-through bonded Acquitex (Texsus, Italy) having basis weight of 50 g/m² was used.
Example 8 b—high loft Vortex (Texsus, Italy) having basis weight of 80 g/m²

Acquisition time under load and rewet value of the fluid absorbent pads are determined and results are summarized in Table 10.

Example 9—Comparative

A fluid-absorbent pad of Example 5 was repeated, except that fluid absorbent polymer particles prepared in example 3 were replaced by commercially available Hysorb®7085 and consists of irregular shaped fluid-absorbent polymer particles produced by gel polymerization exhibiting the following features and absorption profile:
CRC of 30 g/g
SFC of 26 $10^{-7}$ cm³s/g
AUHL of 23 g/g
AUL of 29 g/g
FSC of 46 g/g
Vortex of 68 sec The following acquisition distribution layers were used:
Example 9 a
air-through bonded Acquitex (Texsus, Italy) having basis weight of 50 g/m² was used.
Example 9 b—high loft Vortex (Texsus, Italy) having basis weight of 80 g/m²

Acquisition time under load and rewet value of the fluid absorbent pads are determined and results are summarized in Table 10.

Example 10

A fluid-absorbent pad of Example 5 c was repeated, except that amount of fluid absorbent polymer particles prepared in example 3 were reduced by 10%. The basis weight of the core is 456 g/m². The fluid-absorbent core holds 62.5% by weight uniformly distributed fluid-absorbent polymer particles from Example 3; the quantity of the fluid-absorbent polymer particles within the fluid-absorbent core is 11.7 g.

Acquisition time under load and rewet value of the fluid absorbent pads are determined and results are summarized in Table 10.

Example 11

A fluid-absorbent pad of Example 5 c was repeated, except that amount of fluid absorbent polymer particles prepared in example 3 were reduced by 20%. The basis weight of the core is 424 g/m². The fluid-absorbent core holds 59.8% by weight uniformly distributed fluid-absorbent polymer particles from Example 3; the quantity of the fluid-absorbent polymer particles within the fluid-absorbent core is 10.4 g.

Acquisition time under load and rewet value of the fluid absorbent pads are determined and results are summarized in Table 10.

Example 12

A fluid-absorbent pad of Example 5 c was repeated, except that amount of fluid absorbent polymer particles prepared in example 3 were reduced by 30%. The basis weight of the core is 393 g/m$^2$. The fluid-absorbent core holds 56.5% by weight uniformly distributed fluid-absorbent polymer particles from Example 3; the quantity of the fluid-absorbent polymer particles within the fluid-absorbent core is 9.1 g.

Acquisition time under load and rewet value of the fluid absorbent pads are determined and results are summarized in Table 10.

Example 13

A fluid-absorbent pad of Example 5 was repeated, except that fluid absorbent polymer particles prepared in example 3 were replaced by fluid absorbent polymer particles prepared in example The following acquisition distribution layers were used:

Example 13 a (comparative)-air-through bonded Acquitex (Texsus, Italy) having basis weight of 50 g/m$^2$ Example 13 b—high loft Vortex (Texsus, Italy) having basis weight of 80 g/m$^2$ Example 13 c—high loft Vortex (Texsus, Italy) having basis weight of 100 g/m$^2$ Acquisition time under load and rewet value of the fluid absorbent pads are determined and results are summarized in Table 10.

TABLE 10

| | Rewet under load, acquisition times for each liquid insult into the pads | | | | | | | | | |
|---|---|---|---|---|---|---|---|---|---|---|
| Pad | | | REWET UNDER LOAD [g] | | | | Liquid Acquisition Time [sec] | | | |
| Example | SAP type | ADL | RUL 1 | RUL 2 | RUL 3 | RUL 4 | A1 | A2 | A3 | A4 |
| 5 b | Example 3 | multifunctional 80 gsm | 0.1 | 2.8 | 6.4 | 19.5 | 54 | 80 | 88 | 98 |
| 5 c | Example 3 | vortex 80 gsm | 0.1 | 0.6 | 2.8 | 12.1 | 49 | 70 | 74 | 83 |
| 5 d | Example 3 | vortex 100 gsm | 0.1 | 0.3 | 1.1 | 12.8 | 31 | 41 | 48 | 51 |
| 6 b* | Example 2 | multifunctional 80 gsm | 0.1 | 0.1 | 0.8 | 5.6 | 52 | 75 | 85 | 91 |
| 6 c* | Example 2 | vortex 80 gsm | 0.1 | 0.1 | 0.3 | 3.8 | 48 | 70 | 78 | 84 |
| 6 d* | Example 2 | vortex 100 gsm | 0.1 | 0.2 | 0.3 | 1.4 | 29 | 43 | 50 | 53 |
| 7* b | Example 4 | multifunctional 80 gsm | 0.1 | 0.3 | 1.1 | 11.2 | 54 | 71 | 78 | 82 |
| 7* c | Example 4 | vortex 80 gsm | 0.1 | 0.3 | 1.0 | 9.9 | 48 | 65 | 68 | 75 |
| 7* d | Example 4 | vortex 100 gsm | 0.1 | 0.3 | 2.6 | 11.1 | 28 | 34 | 40 | 42 |
| 8 a* | Hysorb ® 9700 | ATB 50 gsm | 0.1 | 6.5 | 15.6 | 25.0 | 69 | 91 | 110 | 114 |
| 9 a* | Hysorb ® 7085 | ATB 50 gsm | 0.1 | 5.8 | 11.2 | 18.7 | 75 | 112 | 128 | 134 |
| 5 a* | Example 3 | ATB 50 gsm | 0.1 | 2.8 | 7.7 | 15.8 | 96 | 154 | 173 | 189 |
| 6 a* | Example 2 | ATB 50 gsm | 0.1 | 0.6 | 3.6 | 8.8 | 80 | 138 | 152 | 164 |
| 7 a* | Example 4 | ATB 50 gsm | 0.1 | 1.8 | 6.8 | 17.6 | 93 | 150 | 154 | 159 |
| 8 b* | Hysorb ® 9700 | vortex 80 gsm | 0.1 | 7.2 | 17.3 | 31.0 | 41 | 48 | 54 | 58 |
| 9 b* | Hysorb ® 7085 | vortex 80 gsm | 0.1 | 3.2 | 12.3 | 25.1 | 38 | 45 | 56 | 62 |
| 10 | Example 3 | vortex 80 gsm | 0.1 | 0.5 | 3.2 | 12.5 | 47 | 68 | 72 | 82 |
| 11 | Example 3 | vortex 80 gsm | 0.1 | 0.6 | 4.2 | 12.8 | 50 | 69 | 78 | 84 |
| 12 | Example 3 | vortex 80 gsm | 0.1 | 1.9 | 7.6 | 19.7 | 49 | 68 | 78 | 84 |
| 13 a* | Example 1 | ATB 50 gsm | 0.1 | 4.4 | 9.5 | 14.6 | 134 | 257 | 286 | 300** |
| 13 b | Example 1 | vortex 80 gsm | 0.1 | 0.3 | 2.4 | 8.5 | 50 | 75 | 84 | 98 |
| 13 c | Example 1 | vortex 100 gsm | 0.1 | 0.2 | 1.3 | 6.8 | 32 | 45 | 52 | 59 |

*comparative examples

ATB means air-through bonded

**maximum measurement time is 300 s; after 300 s not all solution was absorbed

The fluid-absorbent cores comprising non-surface post-crosslinked fluid-absorbent polymer particles with an SFC of less than $5\times10^{-7}$ cm$^3$s/g (non-permeable), an AUHL of less than 15 g/g in combination with ADLs having high basis weight of at least 70 gsm, preferably at least 80 gsm, show at least comparable or even better rewet and/or liquid acquisition time, in comparison to the fluid-absorbent core containing surface post-cross-linked fluid-absorbent particles in combination with ADL of a basis weight less than 70 gsm.

The invention claimed is:

1. A fluid-absorbent article, comprising:
   (A) an upper liquid-pervious layer;
   (B) a lower liquid-impervious layer;
   (C) a fluid-absorbent core between (A) and (B) comprising at least 60% by weight of non-surface-crosslinked fluid-absorbent polymer particles and not more than 40% by weight of fibrous material, based on a sum of non-surface-crosslinked fluid-absorbent polymer particles and fibrous material, wherein the non-surface-crosslinked fluid-absorbent polymer particles are internally crosslinked;
   (D) an acquisition-distribution layer between (A) and (C) comprising at least 90% by weight of synthetic fibers and not more than 10% by weight of cellulose based fibers, based on a sum of synthetic fibers and cellulose based fibers; and
   (E) an optional tissue layer disposed immediately above and/or below (C);
   wherein a basis weight of the acquisition-distribution layer (D) is at least 80 gsm and the non-surface-crosslinked fluid-absorbent polymer particles have a saline flow conductivity (SFC) of less than $5\times10^{-7}$ cm$^3$s/g and an AUHL of less than 15 g/g;
   wherein the fluid-absorbent polymer particles have a centrifuge retention capacity of at least 35 g/g; and
   wherein the acquisition-distribution layer (D) comprises at least two layers and wherein the acquisition-distribution layer (D) is a non-woven web comprising a three dimensional network of fibers and the network comprises bicomponent fibers and/or polyethylene fibers and/or polypropylene fibers and/or polyester fibers,
   wherein the non-surface-crosslinked fluid-absorbent polymer particles have a level of extractable constituents of less than 8% by weight.

2. The fluid-absorbent article according to claim 1, wherein the basis weight of the acquisition-distribution layer is at least 90 gsm.

3. The fluid-absorbent article according to claim 1, wherein the fluid-absorbent polymer particles have a saline flow conductivity (SFC) of $3\times10^{-7}$ cm$^3$s/g or less.

4. The fluid-absorbent article according to claim 1, wherein the acquisition-distribution layer (D) is air-through bonded.

5. The fluid-absorbent article according to claim 1, wherein the fluid-absorbent core comprises at least 80% by weight of the fluid-absorbent polymer particles.

6. The fluid-absorbent article according to claim 1, wherein the fluid-absorbent polymer particles within the core are placed in discrete regions.

7. The fluid-absorbent article according to claim 1, wherein the fluid-absorbent polymer particles have a centrifuge retention capacity of at least 40 g/g.

8. The fluid-absorbent article according to claim 1, wherein the non-surface-crosslinked fluid-absorbent polymer particles have a mean sphericity of at least 0.8.

9. The fluid-absorbent article according to claim 1, wherein the non-surface-crosslinked fluid-absorbent polymer particles are internally crosslinked with an acrylated glyceryl crosslinker.

10. The fluid-absorbent article according to claim 1, wherein the non-surface-crosslinked fluid-absorbent polymer particles have a level of extractable constituents of less than 5% by weight.

11. The fluid-absorbent article according to claim 1, wherein the non-surface-crosslinked fluid-absorbent polymer particles have a level of extractable constituents of less than 3% by weight.

* * * * *